United States Patent
Yasuma et al.

(10) Patent No.: US 8,153,694 B2
(45) Date of Patent: Apr. 10, 2012

(54) CYCLOPROPANECARBOXYLIC ACID COMPOUND

(75) Inventors: Tsuneo Yasuma, Osaka (JP); Nobuyuki Negoro, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 1047 days.

(21) Appl. No.: 11/989,748

(22) PCT Filed: Jul. 28, 2006

(86) PCT No.: PCT/JP2006/315444
§ 371 (c)(1),
(2), (4) Date: Jan. 28, 2008

(87) PCT Pub. No.: WO2007/013689
PCT Pub. Date: Feb. 1, 2007

(65) Prior Publication Data
US 2010/0144806 A1  Jun. 10, 2010

(30) Foreign Application Priority Data
Jul. 29, 2005  (JP) ................................. 2005-222010

(51) Int. Cl.
*A61K 31/19* (2006.01)
(52) U.S. Cl. ...................................................... 514/572
(58) Field of Classification Search .................... 514/572
See application file for complete search history.

(56) References Cited

U.S. PATENT DOCUMENTS

| 2003/0207924 A1 | 11/2003 | Cheng et al. |
| 2007/0054902 A1 | 3/2007 | Fukui et al. |

FOREIGN PATENT DOCUMENTS

| WO | WO-02/053547 A1 | 7/2002 |
| WO | WO-02/076959 A1 | 10/2002 |
| WO | WO-03/074050 A1 | 9/2003 |
| WO | WO-2004/041266 A1 | 5/2004 |
| WO | WO-2005/019151 A1 | 3/2005 |
| WO | WO-2005/051890 A1 | 6/2005 |
| WO | WO-2005/054213 A1 | 6/2005 |
| WO | WO-2005/063725 A1 | 7/2005 |
| WO | WO-2005/063729 A1 | 7/2005 |

OTHER PUBLICATIONS

Supplemental European Search Report for corresponding European Application No. EP 06 78 2304 dated Jun. 16, 2010.

*Primary Examiner* — San-Ming Hui
(74) *Attorney, Agent, or Firm* — Edwards Wildman Palmer LLP; David G. Conlin; Weiying Yang

(57) ABSTRACT

A compound of the formula (I):

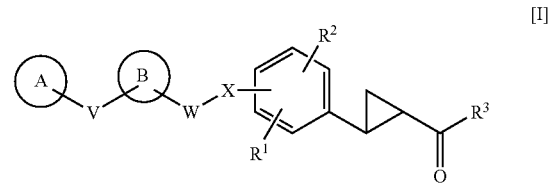

wherein each symbol is as defined in the description, a salt thereof, and a prodrug thereof of the present invention unexpectedly have a superior GPR40 receptor agonist activity and superior properties as pharmaceutical products such as stability and the like, and can be safe and useful pharmaceutical agents for the prophylaxis or treatment of GPR40 receptor-related pathology or diseases in mammals.

17 Claims, No Drawings

CYCLOPROPANECARBOXYLIC ACID COMPOUND

CROSS-REFERENCE TO RELATED APPLICATIONS

This application is the 35 U.S.C. §371 National Stage of PCT Application No. PCT/JP2006/315444, filed Feb. 1, 2007, which claims priority to Japanese Patent Application No. 222010/2005, filed Jul. 29, 2005. The contents of these applications are incorporated herein by reference in their entirety.

TECHNICAL FIELD

The present invention relates to a novel compound having a GPR40 receptor function modulating action, which is useful as an agent for the treatment of diabetes.

BACKGROUND ART

It has been reported in recent years that a ligand of GPR40, which is one of the G Protein-Coupled Receptors (GPCR), is fatty acid and GPR40 in pancreatic β cell is deeply involved in insulin secretion action (Nature, 2003, vol. 422, pages 173-176). Thus, a GPR40 agonist promotes insulin secretion, a GPR40 antagonist inhibits insulin secretion, and the agonist and the antagonist are useful as a therapeutic agent for type 2 diabetes, obesity, impaired glucose tolerance, insulin resistance, neurodegenerative diseases (Alzheimer's disease) and the like (see WO03/068959 and WO02/057783).

In contrast, there are many carboxylic acid compounds reported to be useful as therapeutic agents for various disease.

For example, WO2004/041266 discloses that a compound having an aromatic ring and a group capable of releasing cation is useful as a GPR40 receptor function regulator.

WO03/074050 discloses that a compound represented by formula:

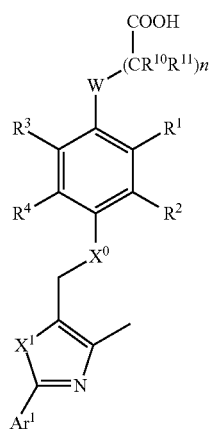

wherein
W is O, S, $CR^5R^6$, $(CH_2)_p$-cycloalkylene or $(CH_2)_p$-heterocycloalkylene wherein p is 0 to 2;.
$X^0$ and $X^1$ are each 0 or S;
$Ar^1$ is an optionally substituted aryl or an optionally substituted heteroaryl;
$R^1$, $R^2$, $R^3$ and $R^4$ are each an hydrogen atom and the like; and n is 0 to 5,
is useful as a PPAR activity regulating agent.

U.S. Pat. No. 6,242,493 discloses that a compound represented by formula:

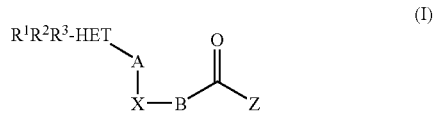

wherein
HET is a 5- to 12-membered monocyclic or bicyclic aromatic ring system;
A is W, CO, $C(R^7)_2$—W wherein W is O, S(O)n and the like, and the like;
$R^1$, $R^2$ and $R^3$ are each a hydrogen atom, a halogen, a lower alkenyl-HET$(R^a)_{4-9}$ and the like;
X is an optionally substituted 5- to 10-membered monocyclic or bicyclic aryl or an optionally substituted heteroaryl, and A and B are bonded to the aryl or heteroaryl both at the ortho positions;
Y is O, $S(O)_n$, $NR^{17}$, a bond or $—CR^{18}=CR^{18}$;
B is $—(C(R^{18})_2)_p—Y—(C(R^{18})_2)_q—$ wherein p and q are each 0 to 3, and when Y is O, S(O)n, $NR^{17}$, a bond or $—CR^{18}=CR^{18}$, then p+q should be 0 to 6, and when Y is a bond, then p+q should be 1 to 6; and
Z is OH or $NHSO_2R^{19}$ wherein $R^{19}$ is a lower alkyl, a lower alkenyl and the like,
is a prostaglandin receptor ligand, and useful for the treatment of pain and the like.

WO2005/019151 discloses that a compound represented by formula:

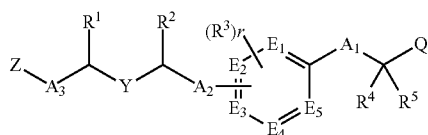

wherein
$A_1$ is a bond, $CH_2$, O or S, and when $A_1$ is $CH_2$, then $A_1$ optionally forms a 3- to 6-membered carbon ring together with $R^4$ or $R^5$;
$A_2$ and $A_3$ are each O or S;
$E_1$, $E_2$, $E_3$, $E_4$ and $E_5$ are each CH or carbon substituted by $A_2$ or $R^3$, and at least one of them is nitrogen;
Q is $C(O)OR^6$ wherein $R^6$ is a hydrogen atom or a $C_{1-6}$ alkyl, and the like;
Y is a bond, a $C_{1-6}$ alkyl or a $C_{3-6}$ cycloalkyl;
Z is aryl, 5- to 10-membered heteroaryl and the like;
r is 1 to 4;
$R^1$ and $R^2$ are each a hydrogen atom, a $C_{1-6}$ alkyl and the like;
$R^3$ is a hydrogen atom and the like; and
$R^4$ and $R^5$ are each a hydrogen atom or a $C_{1-6}$ alkyl, is a PPAR agonist.

WO02/053547 discloses that a compound represented by formula:

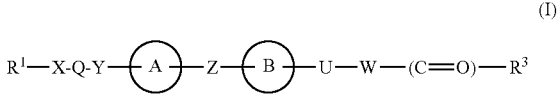

wherein
R¹ is an optionally substituted 5-membered aromatic heterocyclic group;
X is a bond and the like;
Q is a $C_{1-20}$ divalent hydrocarbon group;
Y is a bond and the like;
ring A is an optionally substituted aromatic ring;
Z is —$(CH_2)$n-$Z^1$— or —$Z^1$—$(CH_2)$n- wherein n is 1 to 8, $Z^1$ is O and the like;
ring B is an optionally substituted pyridine, an optionally substituted benzene or an optionally substituted naphthalene;
U is a bond and the like;
W is a $C_{1-20}$ divalent hydrocarbon group; and
R³ is a hydroxyl and the like,
is a PPAR ligand, and useful for the prophylaxis or treatment of diabetes and the like.

WO02/076959 discloses that a compound represented by formula:

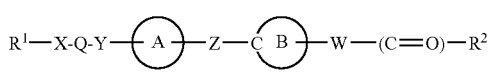

(I)

wherein
R¹ is an optionally substituted 5-membered heterocyclic group;
X and Y are each a bond, O, S and the like;
Q is a divalent $C_{1-20}$ hydrocarbon group;
ring A is an aromatic ring optionally further having 1 to 3 substituents;
Z is —$(CH_2)_n$—$Z^1$— or —$Z^1$—$(CH_2)_n$— wherein n is 1-8; and $Z_1$ is O and the like;
ring B is a 5-membered heterocycle optionally further having 1 to 3 substituents;
W is a divalent $C_{1-20}$ saturated hydrocarbon group; and
R² is —$OR^8$ wherein R⁸ is a hydrogen atom or an optionally substituted hydrocarbon group, and the like,
is a PPAR ligand, and useful for the prophylaxis or treatment of diabetes and the like.

However, none of the above-mentioned prior art reports on the compound of the present invention.

DISCLOSURE OF THE INVENTION

The present invention aims at providing a novel compound having a GPR40 receptor function modulating action, which is useful as an insulin secretagogue or an agent for the prophylaxis or treatment of diabetes and the like.

The present inventors have intensively conducted various studies and found that a compound represented by the formula (I):

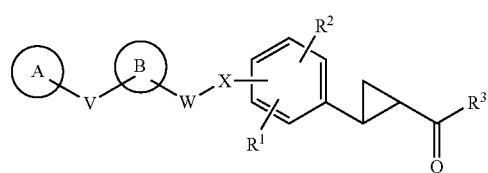

[I]

wherein
ring A is an optionally substituted cyclic group;
ring B is an optionally substituted ring;
V is a bond or a spacer having 1 to 3 atoms in the main chain;
W is an optionally substituted $C_{1-6}$ alkylene group;
X is O or S;
R¹ and R² are the same or different and each is a hydrogen atom, a halogen atom, a $C_{1-6}$ alkyl group or a $C_{1-6}$ alkoxy group; and
R³ is an optionally substituted hydroxy group or an optionally substituted amino group,
provided that when V is a bond and W is a methylene group, then ring B should not be oxazole and thiazole,
or a salt thereof, excluding 2-(2-{[6-(benzyloxy)-2-naphthyl]methoxy}phenyl)cyclopropanecarboxylic acid [hereinafter sometimes to be abbreviated as compound (I)], which is characterized by a chemical structure wherein a substituted carbonyl-cycloalkyl group is bonded to the benzene ring, unexpectedly has a superior GPR40 receptor agonist activity, shows superior properties as a pharmaceutical product such as stability and the like, and can be a safe and useful pharmaceutical agent for the prophylaxis or treatment of GPR40 receptor related pathology or diseases in mammals, and completed the present invention based on these findings.

Accordingly, the present invention relates to

[1] compound (I);
[2] a prodrug of compound (I);
[3] compound (I) wherein ring B is an optionally substituted benzene ring;
[4] compound (I) wherein ring A is an optionally substituted phenyl;
[5] compound (I) wherein ring A is an optionally substituted thiazolyl;
[6] compound (I) wherein V is
(1) a bond;
(2) —$W^3$—$N(R^4)$—$W^2$—; or
(3) —$W^3$—O—$W^2$—
wherein
$W^2$ and $W^3$ are the same or different and each is a bond or an optionally substituted linear $C_{1-2}$ alkylene group, and when both of $W^2$ and $W^3$ are optionally substituted linear $C_{1-2}$ alkylene groups, then the total carbon number of the linear $C_{1-2}$ alkylene groups constituting $W^2$ and $W^3$ should be 2, and $R^4$ is a hydrogen atom or a substituent;
[7] compound (I) wherein W is —$CH_2$—;
[8] compound (I) wherein X is O;
[9] compound (I) wherein R¹ and R² are each a hydrogen atom or a halogen atom;
[10] compound (I) wherein R³ is a hydroxy group;
[11] compound (I) which is selected from
2-(4-{[4'-(2-ethoxyethoxy)-2',6'-dimethylbiphenyl-3-yl]methoxy}phenyl)cyclopropanecarboxylic acid,
2-[4-({4'-[(1,1-dioxidotetrahydro-2H-thiopyran-4-yl)oxy]-2',6'-dimethylbiphenyl-3-yl}methoxy)phenyl]cyclopropanecarboxylic acid,
2-[4-({2',6'-dimethyl-4'-[(3-methyloxetan-3-yl)methoxy]biphenyl-3-yl}methoxy)phenyl]cyclopropanecarboxylic acid,
2-[4-({4-[((3-methylbutyl){4-[4-(trifluoromethyl)phenyl]-1,3-thiazol-2-yl}amino)methyl]benzyl}oxy)phenyl]cyclopropanecarboxylic acid,
2-[4-({4-[(propyl{4-[4-(trifluoromethyl)phenyl]-1,3-thiazol-2-yl}amino)methyl]benzyl}oxy)phenyl]cyclopropanecarboxylic acid, and salts thereof;
[12] an insulin secretagogue comprising compound (I) or a prodrug thereof;
[13] a pharmaceutical agent comprising compound (I) or a prodrug thereof;

[14] an agent for the prophylaxis or treatment of a pathology or disease involving a GPR40 receptor, which comprises compound (I) or a prodrug thereof;

[15] the pharmaceutical agent of the above-mentioned [13], which is an agent for the prophylaxis or treatment of diabetes;

[16] use of compound (I) or a prodrug thereof for the production of an insulin secretagogue;

[17] use of compound (I) or a prodrug thereof for the production of an agent for the prophylaxis or treatment of a pathology or disease involving a GPR40 receptor;

[18] a method of promoting insulin secretion in a mammal, which comprises administering an effective amount of compound (I) or a prodrug thereof to the mammal;

[19] a method for the prophylaxis or treatment of a pathology or disease involving a GPR40 receptor in a mammal, which comprises administering an effective amount of compound (I) or a prodrug thereof to the mammal; and the like.

The compound of the present invention has a superior GPR40 receptor function modulating action and can be used as an agent for the prophylaxis or treatment of diabetes and the like.

BEST MODE FOR EMBODYING THE INVENTION

Each symbol in the formula (I) is described in detail in the following.

Unless otherwise specified, the "halogen atom" in the present specification means fluorine atom, chlorine atom, bromine atom or iodine atom.

Unless otherwise specified, the "$C_{1-3}$ alkylenedioxy group" in the present specification means methylenedioxy, ethylenedioxy or the like.

Unless otherwise specified, the "$C_{1-6}$ alkyl group" in the present specification means methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

Unless otherwise specified, the "$C_{1-6}$ alkoxy group" in the present specification means methoxy, ethoxy, propoxy, isopropoxy, butoxy, isobutoxy, sec-butoxy, tert-butoxy or the like.

Unless otherwise specified, the "$C_{1-6}$ alkoxy-.carbonyl group" in the present specification means methoxycarbonyl, ethoxycarbonyl, propoxycarbonyl, tert-butoxycarbonyl or the like.

Unless otherwise specified, the "$C_{1-6}$ alkyl-carbonyl group" in the present specification means acetyl, propanoyl, butanoyl, isobutanoyl, pentanoyl, isopentanoyl, hexanoyl or the like.

$R^1$ and $R^2$ are the same or different and each is a hydrogen atom, a halogen atom, a $C_{1-6}$ alkyl group or a $C_{1-6}$ alkoxy group.

$R^1$ and $R^2$ are each preferably a hydrogen atom, a halogen atom (preferably a fluorine atom) or the like.

$R^3$ is an optionally substituted hydroxy group or an optionally substituted amino group.

As the "optionally substituted hydroxy group" for $R^3$, for example, a hydroxy group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a 5- or 6-membered aromatic heterocyclic group, a fused aromatic heterocyclic group and the like, each of which is optionally substituted, can be mentioned.

As the $C_{1-10}$ alkyl group, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like can be mentioned.

As the $C_{2-10}$ alkenyl group, for example, ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like can be mentioned.

As the $C_{3-10}$ cycloalkyl group, for example, cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like can be mentioned.

As the $C_{3-10}$ cycloalkenyl group, for example, 2-cyclopenten-1-yl, 3-cyclopenten-1-yl, 2-cyclohexen-1-yl, 3-cyclohexen-1-yl and the like can be mentioned.

The above-mentioned $C_{3-10}$ cycloalkyl group and $C_{3-10}$ cycloalkenyl group are each optionally condensed with a benzene ring. As such fused cyclic group, for example, indanyl, dihydronaphthyl, tetrahydronaphthyl, fluorenyl and the like s can be mentioned.

As the $C_{6-14}$ aryl group, for example, phenyl, naphthyl, anthryl, phenanthryl, acenaphthyl, biphenylyl and the like can be mentioned.

As the $C_{7-13}$ aralkyl group, for example, benzyl, phenethyl, naphthylmethyl, biphenylylmethyl and the like can be mentioned.

As the $C_{8-13}$ arylalkenyl group, for example, styryl and the like can be mentioned.

As the 5- or 6-membered aromatic heterocyclic group, a 5- or 6-membered cyclic group, from among the "aromatic heterocyclic groups" exemplified as the "heterocyclic group" of the below-mentioned "optionally substituted heterocyclic group" for $R^a$, $R^{a'}$ or $R^{b'}$ (which is mentioned below in specific examples of the acyl group" exemplified as the "substituent" of the "optionally substituted amino group"), can be mentioned.

As the fused aromatic heterocyclic group, a fused cyclic group, from among the "aromatic heterocyclic groups" exemplified as the "heterocyclic group" of the below-mentioned "optionally substituted heterocyclic group" for $R^a$, $R^{a'}$ or $R^{b'}$, can be mentioned.

The aforementioned $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group, $C_{1-6}$ alkyl-carbonyl group, 5- or 6-membered aromatic heterocyclic group and fused aromatic heterocyclic group optionally have 1 to 3 substituents at the substitutable positions. When the number of the substituents is 2 or more, respective substituents may be the same or different.

As the substituents for the $C_{1-10}$ alkyl group, $C_{2-10}$ alkenyl group and $C_{1-6}$ alkyl-carbonyl group, the following substituent can be mentioned:

(1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from a $C_{1-6}$ alkyl group optionally substituted by 1 to 3 halogen atoms, a hydroxy group, a $C_{1-6}$ alkoxy group, a halogen atom and a $C_{1-6}$ alkylsulfonyloxy group (e.g., methylsulfonyloxy);

(3) an aromatic heterocyclic group (e.g., thienyl, furyl, pyridyl, oxazolyl, thiazolyl, tetrazolyl, oxadiazolyl, pyrazinyl, quinolyl, indolyl) optionally substituted by 1 to 3 substituents selected from a $C_{1-6}$ alkyl group optionally substituted by 1 to 3 halogen atoms, a hydroxy group, a $C_{1-6}$ alkoxy group and a halogen atom;

(4) a non-aromatic heterocyclic group (e.g., tetrahydrofuryl, morpholinyl, thiomorpholinyl, piperidinyl, pyrrolidinyl, piperazinyl, dioxolyl, dioxolanyl, 1,3-dihydro-2-benzofuranyl, thiazolidinyl, oxooxadiazolyl) optionally substituted by 1 to 3 substituents selected from a $C_{1-6}$ alkyl group optionally substituted by 1 to 3 halogen atoms, a hydroxy group, a $C_{1-6}$ alkoxy group, an oxo group and a halogen atom;

(5) an amino group optionally mono- or di-substituted by substituent(s) selected from a $C_{1-6}$ alkyl group, a $C_{1-6}$ alkyl-carbonyl group, a $C_{1-6}$ alkoxy-carbonyl group, a $C_{6-14}$ aryl-carbonyl group (e.g., benzoyl), a $C_{7-13}$ aralkyl-carbonyl group (e.g., benzylcarbonyl, phenethylcarbonyl), a $C_{1-6}$ alkyl-carbamoyl group (e.g., methylcarbamoyl, ethylcarbamoyl), a $C_{6-14}$ aryl-carbamoyl group (e.g., phenylcarbamoyl, 1-naphthylcarbamoyl, 2-naphthylcarbamoyl), a $C_{7-13}$ aralkyl-carbamoyl group (e.g., benzylcarbamoyl), a $C_{1-6}$ alkylsulfonyl group (e.g., methylsulfonyl, ethylsulfonyl, isopropylsulfonyl), a $C_{6-14}$ arylsulfonyl group (e.g., benzenesulfonyl, toluenesulfonyl, 1-naphthalenesulfonyl, 2-naphthalenesulfonyl) and a $C_{7-13}$ aralkylsulfonyl group (e.g., benzylsulfonyl);

(6) an amidino group;

(7) a $C_{1-6}$ alkyl-carbonyl group optionally substituted by 1 to 3 halogen atoms;

(8) a $C_{1-6}$ alkoxy-carbonyl group optionally substituted by 1 to 3 halogen atoms;

(9) a $C_{1-6}$ alkylsulfonyl group (e.g., methylsulfonyl) optionally substituted by 1 to 3 halogen atoms;

(10) a carbamoyl group optionally mono- or di-substituted by substituent(s) selected from a $C_{1-6}$ alkyl group optionally substituted by 1 to 3 halogen atoms, a $C_{6-14}$ aryl group (e.g., phenyl), a $C_{7-13}$ aralkyl group (e.g., benzyl) and an aromatic heterocyclyl-$C_{1-6}$ alkyl group (e.g., furfuryl);

(11) a thiocarbamoyl group optionally mono- or di-substituted by $C_{1-6}$ alkyl group(s) optionally substituted by 1 to 3 halogen atoms;

(12) a sulfamoyl group optionally mono- or di-substituted by $C_{1-6}$ alkyl group(s) optionally substituted by 1 to 3 halogen is atoms;

(13) a carboxyl group;

(14) a hydroxy group;

(15) a $C_{1-6}$ alkoxy group optionally substituted by 1 to 3 substituents selected from a halogen atom, a carboxyl group, a $C_{1-6}$ alkoxy group, a $C_{1-6}$ alkoxy-carbonyl group, and a non-aromatic heterocyclic group (e.g., oxetanyl) optionally substituted by $C_{1-6}$ alkyl group(s);

(16) a $C_{2-6}$ alkenyloxy group (e.g., ethenyloxy) optionally substituted by 1 to 3 halogen atoms;

(17) a $C_{1-10}$ cycloalkyloxy group (e.g., cyclohexyloxy);

(18) a $C_{7-13}$ aralkyloxy group (e.g., benzyloxy);

(19) a $C_{6-14}$ aryloxy group (e.g., phenyloxy, naphthyloxy);

(20) a non-aromatic heterocyclyl-oxy group (e.g., tetrahydrothiopyranyl, 1-oxidotetrahydrothiopyranyl, 1,1-dioxidotetrahydrothiopyranyl);

(21) a $C_{1-6}$ alkyl-carbonyloxy group (e.g., acetyloxy, tert-butylcarbonyloxy);

(22) a mercapto group;

(23) a $C_{1-6}$ alkylthio group (e.g., methylthio, ethylthio) optionally substituted by 1 to 3 halogen atoms;

(24) a $C_{7-20}$ aralkylthio group (e.g., benzylthio, tritylthio);

(25) a $C_{6-14}$ arylthio group (e.g., phenylthio, naphthylthio);

(26) a sulfo group;

(27) a cyano group;

(28) an azido group;

(29) a nitro group;

(30) a nitroso group;

(31) a halogen atom;

(32) a $C_{1-6}$ alkylsulfinyl group (e.g., methylsulfinyl);

(33) an oxo group;

(34) a $C_{3-10}$ cycloalkyl-$C_{1-6}$ alkyloxy group (e.g., cyclopropylmethyloxy);

(35) a $C_{1-3}$ alkylenedioxy group;

(36) a hydroxyimino group optionally substituted by a $C_{1-6}$ alkyl group;

and the like.

As the substituents for the $C_{3-10}$ cycloalkyl group, $C_{3-10}$ cycloalkenyl group, $C_{6-14}$ aryl group, $C_{7-13}$ aralkyl group, $C_{8-13}$ arylalkenyl group, 5- or 6-membered aromatic heterocyclic group and fused aromatic heterocyclic group, the following substituents can be mentioned:

(1) those exemplified as the substituents which the aforementioned $C_{1-10}$ alkyl group and the like optionally have;

(2) a $C_{1-6}$ alkyl group optionally substituted by 1 to 3 substituents selected from a halogen atom, a carboxyl group, a hydroxy group, a $C_{1-6}$ alkoxy-carbonyl group, a $C_{1-6}$ alkyl-carbonyloxy group (e.g., acetyloxy, tert-butylcarbonyloxy), a carbamoyl group and a non-aromatic heterocyclic group (e.g., piperidino);

(3) a $C_{2-6}$ alkenyl group (e.g., ethenyl, 1-propenyl) optionally substituted by 1 to 3 substituents selected from a halogen atom, a carboxyl group, a $C_{1-6}$ alkoxy-carbonyl group and a carbamoyl group;

(4) a $C_{7-13}$ aralkyl group (e.g., benzyl) optionally substituted by 1 to 3 substituents selected from a $C_{1-6}$ alkyl group optionally substituted by 1 to 3 halogen atoms, a hydroxy group, a $C_{1-6}$ alkoxy group and a halogen atom; and the like.

As the "optionally substituted amino group" for $R^3$, for example, an amino group optionally substituted by 1 or 2 substituent(s) selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group and a $C_{8-13}$ arylalkenyl group, each of which is optionally substituted; an acyl group and the m like, can be mentioned.

As the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group, those exemplified as the "substituent" of the aforementioned "optionally is substituted hydroxy group" can be mentioned.

The $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group optionally have 1 to 3 substituents at the substitutable positions. When the number of the substituents is 2 or more, respective substituents may be the same or different.

As the substituents for the $C_{1-10}$ alkyl group and $C_{2-10}$ alkenyl group, those exemplified as the "substituents" which the $C_{1-10}$ alkyl group and the like exemplified as the "substituent" of the aforementioned "optionally substituted hydroxy group" optionally have, can be mentioned.

As the substituents for the $C_{3-10}$ cycloalkyl group, $C_{3-10}$ cycloalkenyl group, $C_{6-14}$ aryl group, $C_{7-13}$ aralkyl group and $C_{8-13}$ arylalkenyl group, those exemplified as the "substituents" which the $C_{3-10}$ cycloalkyl group and the like exemplified as the "substituent" of the aforementioned "optionally substituted hydroxy group" optionally have, can be mentioned.

As the "acyl group" exemplified as the substituent of the "optionally substituted amino group", for example, a group represented by the formula: —$COR^a$, —$CO$—$OR^a$, —$SO_2R^a$, —$SOR^a$, —$CO$—$NR^{a'}R^{b'}$ or —$CS$—$NR^{a'}R^{b'}$ wherein $R^a$ is a hydrogen atom, an optionally substituted hydrocarbon group or an optionally substituted heterocyclic group, $R^{a'}$ and $R^{b'}$ are the same or different and each is a hydrogen atom, an optionally substituted hydrocarbon group or an optionally substituted heterocyclic group, or $R^{a'}$ and $R^{b'}$ form an optionally substituted nitrogen-containing heterocycle together with the adjacent nitrogen atom, and the like can be mentioned.

As the "hydrocarbon group" of the "optionally substituted m hydrocarbon group" for $R^a$, $R^{a'}$ or $R^{b'}$, for example, a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{8-14}$ aryl group, a $C_{7-13}$ aralkyl group, a $C_{8-13}$ arylalkenyl group, a $C_{3-10}$ cycloalkyl-$C_{1-6}$ alkyl group and is the like can be mentioned.

As the $C_{1-10}$ alkyl group, $C_{2-10}$ alkenyl group, $C_{3-10}$ cycloalkyl group, $C_{3-10}$ cycloalkenyl group, $C_{8-14}$ aryl group, $C_{7-13}$ aralkyl group and $C_{8-13}$ arylalkenyl group, those exemplified as the "substituent" of the aforementioned "optionally substituted hydroxy group" can be mentioned.

As the $C_{2-10}$ alkynyl group, for example, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like can be mentioned.

As the $C_{4-10}$ cycloalkadienyl group, for example, 2,4-cyclopentadien-1-yl, 2,4-cyclohexadien-1-yl, 2,5-cyclohexadien-1-yl and the like can be mentioned.

As the $C_{3-10}$ cycloalkyl-$C_{1-6}$ alkyl group, for example, cyclohexylmethyl and the like can be mentioned.

The "optionally substituted hydrocarbon group" for $R^a$, $R^{a'}$ or $R^{b'}$ optionally has 1 to 3 substituents at the substitutable positions. As such substituents, those exemplified as the "substituents" which the $C_{3-10}$ cycloalkyl group and the like exemplified as the "substituent" of the aforementioned "optionally substituted hydroxy group" optionally have, can be mentioned. When the number of the substituents is 2 or more, respective substituents may be the same or different.

As the "heterocyclic group" of the "optionally substituted heterocyclic group" for $R^a$, $R^{a'}$ or $R^{b'}$, for example, an aromatic heterocyclic group and a non-aromatic heterocyclic group can be mentioned.

As the aromatic heterocyclic group, for example, a 4- to 7-membered (preferably 5- or 6-membered) monocyclic aromatic heterocyclic group containing, as a ring-constituting atom besides carbon atoms, 1 to 4 hetero atom selected from an oxygen atom, a sulfur atom and a nitrogen atom ring, and a fused aromatic heterocyclic group can be mentioned. As the fused aromatic heterocyclic group, for example, a group derived from a fused ring wherein a ring constituting such 4- to 7- membered monocyclic aromatic heterocyclic group, and 1 or 2 rings selected from a 5- or 6-membered ring containing 1 or 2 nitrogen atoms, a 5-membered ring containing one sulfur atom, a benzene ring and the like are condensed, and the like can be mentioned.

As the preferable examples of the aromatic heterocyclic group,
monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like; fused aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g.,pyrazolo[5,1-c][1,2,4]triazin-3-yl) and the like; and the like can be mentioned.

As the non-aromatic heterocyclic group, for example, a 4- to 7-membered (preferably 5- or 6-membered) monocyclic non-aromatic heterocyclic group containing, as a ring-constituting atom, besides carbon atoms, 1 to 4 hetero atom selected from an oxygen atom, a sulfur atom and a nitrogen atom, and a fused non-aromatic heterocyclic group can be mentioned. As the fused non-aromatic heterocyclic group, for example, a group derived from a fused ring wherein a ring constituting such 4- to 7-membered monocyclic non-aromatic heterocyclic group, and 1 or 2 rings selected from a 5- or 6-membered ring containing 1 or 2 nitrogen atoms, a 5-membered ring containing one sulfur atom, a benzene ring and the like are condensed, and the like can be mentioned.

As the preferable examples of the non-aromatic heterocyclic group,
monocyclic non-aromatic heterocyclic groups such as pyrrolidinyl (e.g., 1-pyrrolidinyl, 2-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), piperazinyl (e.g., 1-piperazinyl, 2-piperazinyl), hexamethyleniminyl (e.g., hexamethyleneimin-1-yl), oxazolidinyl (e.g., oxazolidin-2-yl), thiazolidinyl (e.g., thiazolidin-2-yl), imidazolidinyl (e.g., imidazolidin-1-yl, imidazolidin-2-yl), oxazolinyl (e.g., oxazolin-2-yl), thiazolinyl (e.g., thiazolin-2-yl), imidazolinyl (e.g., imidazolin-1-yl, imidazolin-2-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), 2-thioxo-1,3-oxazolidin-5-yl, pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl) and the like; fused non-aromatic heterocyclic groups such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydrobenzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydrobenzofuran-3-yl), chromenyl (e.g., 4H-chromen-2-yl, 2H-chromen-3-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl) and the like; and the like can be mentioned.

The "heterocyclic group" of the aforementioned "optionally substituted heterocyclic group" optionally has 1 to 3 substituents at the substitutable positions. As such substituents, for example, those exemplified as the "substituents" which the $C_{3-10}$ cycloalkyl group and the like exemplified as the "substituent" of the aforementioned "optionally substituted hydroxy group" optionally have, can be mentioned. When the number of the substituents is 2 or more, respective substituents may be the same or different.

As the "nitrogen-containing heterocycle" of the "optionally substituted nitrogen-containing heterocycle" formed by $R^{a'}$ and $R^{b'}$ together with the adjacent nitrogen atom, for example, a 5- to 7-membered nitrogen-containing heterocycle containing, as a ring-constituting atom besides carbon atoms, at least one nitrogen atom and optionally further containing 1 to 2 hetero atoms selected from an oxygen atom, a sulfur atom and a nitrogen atom, can be mentioned. As the preferable examples of the nitrogen-containing heterocycle, pyrrolidine, imidazolidine, pyrazolidine, piperidine, piperazine, morpholine, thiomorpholine, oxopiperazine and the like can be mentioned.

The nitrogen-containing heterocycle optionally has 1 to 3 (preferably 1 to 2) substituents at the substitutable positions. As such substituents, those exemplified as the "substituents" which the $C_{3-10}$ cycloalkyl group and the like s exemplified as the "substituent" of the aforementioned "optionally substituted hydroxy group" optionally have, can be mentioned. When the number of the substituents is 2 or more, respective substituents may be the same or different.

As the preferable examples of the "acyl group",
(1) a formyl group;
(2) a carboxyl group;
(3) a $C_{1-6}$ alkyl-carbonyl group;
(4) a $C_{1-6}$ alkoxy-carbonyl group optionally substituted by 1 to 3 substituents selected from a carboxyl group, a carbamoyl group, a thiocarbamoyl group, a $C_{1-6}$ alkoxy-carbonyl group and a $C_{1-6}$ alkyl-carbonyloxy group (e.g., methoxycarbonyl, ethoxycarbonyl, propoxycarbonyl, tert-butoxycarbonyl; carboxymethoxycarbonyl, carboxyethoxycarbonyl, carboxybutoxycarbonyl; carbamoylmethoxycarbonyl; thiocarbamoylmethoxycarbonyl; ethoxycarbonylmethoxycarbonyl, ethoxycarbonylethoxycarbonyl, methoxycarbonylbutoxycarbonyl, ethoxycarbonylbutoxycarbonyl; tert-butylcarbonyloxymethoxycarbonyl);
(5) a $C_{3-10}$ cycloalkyl-carbonyl group (e.g., cyclopentylcarbonyl, cyclohexylcarbonyl);
(6) a $C_{6-14}$ aryl-carbonyl group (e.g., benzoyl, 1-naphthoyl, 2-naphthoyl) optionally substituted by 1 to 3 substituents selected from a halogen atom, a cyano group, an optionally halogenated $C_{1-6}$ alkyl group (i.e., a $C_{1-6}$ alkyl group optionally substituted by 1 to 3 halogen atoms), a $C_{1-6}$ alkoxy group, a carboxyl group, a $C_{1-6}$ alkoxy-carbonyl group, an aromatic heterocyclic group (e.g., tetrazolyl, oxadiazolyl), a non-aromatic heterocyclic group (e.g., oxooxadiazolyl) and a carbamoyl group;
(7) a $C_{6-14}$ aryloxy-carbonyl group (e.g., phenyloxycarbonyl, naphthyloxycarbonyl) optionally substituted by 1 to 3 substituents selected from a carboxyl group, a $C_{1-6}$ alkoxy-carbonyl group and a carbamoyl group;
(8) a $C_{7-13}$ aralkyloxy-carbonyl group optionally substituted by 1 to 3 substituents selected from a carboxyl group, a carbamoyl group, a thiocarbamoyl group, a $C_{1-6}$ alkoxy-carbonyl group, a halogen atom, a cyano group, a nitro group, a $C_{1-6}$ alkoxy group, a $C_{1-6}$ alkylsulfonyl group and a $C_{1-6}$ alkyl group (e.g., benzyloxycarbonyl, phenethyloxycarbonyl; carboxybenzyloxycarbonyl; methoxycarbonylbenzyloxycarbonyl; biphenylylmethoxycarbonyl);
(9) a carbamoyl group optionally mono- or di-substituted by $C_{1-6}$ alkyl group(s) optionally substituted by 1 to 3 substituents selected from a halogen atom and a $C_{1-6}$ alkoxy group (e.g., methylcarbamoyl, ethylcarbamoyl, dimethylcarbamoyl, diethylcarbamoyl, ethylmethylcarbamoyl, propylcarbamoyl, isopropylcarbamoyl, butylcarbamoyl, isobutylcarbamoyl, trifluoroethylcarbamoyl, N-methoxyethyl-N-methylcarbamoyl);
(10) a $C_{1-6}$ alkylsulfonyl group optionally substituted by 1 to 3 substituents selected from a carboxyl group, a carbamoyl group and a $C_{1-6}$ alkoxy-carbonyl group (e.g., methylsulfonyl, carboxymethylsulfonyl);
(11) a $C_{1-6}$ alkylsulfinyl group (e.g., methylsulfinyl);
(12) a thiocarbamoyl group;
(13) a $C_{7-13}$ aralkyl-carbonyl group (e.g., benzylcarbonyl, phenethylcarbonyl);
(14) an aromatic heterocyclyl-carbonyl group (e.g., furylcarbonyl, thienylcarbonyl, thiazolylcarbonyl, pyrazolylcarbonyl, pyridylcarbonyl, pyrazinylcarbonyl, benzofuranylcarbonyl, benzothienylcarbonyl, quinoxalinylcarbonyl) optionally substituted by 1 to 3 substituents selected from a $C_{1-6}$ alkyl group, a $C_{6-14}$ aryl group, a $C_{7-13}$ aralkyl group, a $C_{1-6}$ alkoxy group, a carboxyl group, a $C_{1-6}$ alkoxy-carbonyl group and a carbamoyl group; and the like can be mentioned.

$R^3$ is preferably an optionally substituted hydroxy group and the like, more preferably a hydroxy group, a $C_{1-10}$ alkoxy group and the like, particularly preferably a hydroxy group.

Ring A is an optionally substituted cyclic group. As the "cyclic group" of the "optionally substituted cyclic group" for ring A, for example, an aromatic group, a non-aromatic cyclic group and the like can be mentioned.

As the aromatic group, for example, an aromatic hydrocarbon group, an aromatic heterocyclic group and the like can be mentioned.

As the aromatic hydrocarbon group, for example, a $C_{6-14}$ aryl group and the like can be mentioned. As the $C_{6-14}$ aryl group, those exemplified as the "substituent" of the aforementioned "optionally substituted hydroxy group" for $R^3$ can be mentioned. As the aromatic heterocyclic group, those exemplified as the "heterocyclic group" of the aforementioned "optionally substituted heterocyclic group" $R^a$, $R^{a'}$ or $R^{b'}$ can be mentioned.

As the non-aromatic cyclic group, for example, a non-aromatic cyclic hydrocarbon group, a non-aromatic heterocyclic group and the like can be mentioned.

As the non-aromatic cyclic hydrocarbon group, for example, a $C_{3-10}$ cycloalkyl group, a $C_{3-10}$ cycloalkenyl group and a $C_{4-10}$ cycloalkadienyl group, each of which is optionally condensed with a benzene ring, and the like can be mentioned. As the $C_{3-10}$ cycloalkyl group and $C_{3-10}$ cycloalkenyl group, those exemplified as the "substituent" of the aforementioned "optionally substituted hydroxy group" for $R^3$ can be mentioned. cycloalkadienyl group, those exemplified as the "hydrocarbon group" of the aforementioned "optionally substituted hydrocarbon group" $R^a$, $R^{a'}R^{b'}$ can be mentioned.

As the non-aromatic heterocyclic group, those exemplified as the "heterocyclic group" of the aforementioned "optionally substituted heterocyclic group" $R^a$, $R^{a'}$, or $R^{b'}$ can be mentioned.

The "cyclic group" of the "optionally substituted cyclic group" for ring A is preferably an aromatic hydrocarbon group (preferably phenyl), an aromatic heterocyclic group (preferably thiazolyl) and the like, more preferably phenyl, thiazolyl and the like.

The "cyclic group" of the "optionally substituted cyclic group" for ring A optionally has 1 to 3 substituents at the substitutable positions. As such substituents, those exemplified as the "substituents" which the $C_{3-10}$ cycloalkyl group and the like exemplified as the "substituent" of the "optionally substituted hydroxy group" for $R^3$ optionally have, can be mentioned. When the number of the substituents is 2 or more, respective substituents may be the same or different.

As the preferable substituents of ring A,
(1) a $C_{1-6}$ alkyl group;
(2) a $C_{1-6}$ alkoxy group optionally substituted by 1 to 3 substituents selected from
    (a) a $C_{1-6}$ alkoxy group,
    (b) a non-aromatic heterocyclic group (e.g., oxetanyl) optionally substituted by $C_{1-6}$ alkyl group(s) and the like;
(3) a non-aromatic heterocyclyloxy group (e.g., tetrahydrothiopyranyloxy, 1-oxidotetrahydrothiopyranyloxy, 1,1-dioxidotetrahydrothiopyranyloxy);
(4) a $C_{6-14}$ aryl group (e.g., phenyl, naphthyl) optionally substituted by $C_{1-6}$ alkyl group(s) optionally substituted by 1 to 3 halogen atoms; and the like can be mentioned.

Ring A is preferably an optionally substituted aromatic hydrocarbon group (preferably phenyl), an optionally substituted aromatic heterocyclic group (preferably thiazolyl) and the like, more preferably an aromatic hydrocarbon group (preferably phenyl), an aromatic heterocyclic group (preferably thiazolyl) and the like, each of which is optionally substituted by 1 to 3 substituents selected from
(1) a $C_{1-6}$ alkyl group;
(2) a $C_{1-6}$ alkoxy group optionally substituted by 1 to 3 substituents selected from
    (a) a $C_{1-6}$ alkoxy group,
    (b) a non-aromatic heterocyclic group (e.g., oxetanyl) optionally substituted by $C_{1-6}$ alkyl group(s) and the like;
(3) a non-aromatic heterocyclyloxy group (e.g., tetrahydrothiopyranyloxy, 1-oxidotetrahydrothiopyranyloxy, 1,1-dioxidotetrahydrothiopyranyloxy);
(4) a $C_{6-14}$ aryl group (e.g., phenyl, naphthyl) optionally substituted by $C_{1-6}$ alkyl group(s) optionally substituted by 1 to 3 halogen atoms; and the like.

Ring B is an optionally substituted ring. As the "ring" of the "optionally substituted ring" for ring B, for example, rings constituting groups exemplified as the "cyclic group" of the "optionally substituted cyclic group" for ring A, and the like can be mentioned.

The "ring" of the "optionally substituted ring" for ring B is preferably an aromatic hydrocarbon (preferably benzene) and the like.

The "ring" of the "optionally substituted ring" for ring B optionally further has 1 to 3 substituents at the substitutable position, besides the group V and the group W. As such substituents, those exemplified as the "substituents" which the $C_{3-10}$ cycloalkyl group and the like exemplified as the "substituent" of the "optionally substituted hydroxy group" for $R^3$ optionally have, can be mentioned. When the number of the substituents is 2 or more, respective substituents may be the same or different.

Ring B is preferably an aromatic hydrocarbon (preferably benzene) and the like, more preferably benzene.

V is a bond or a spacer having 1 to 3 atoms in the main chain. The "main chain" is a divalent straight chain connecting ring A and ring B, and the "atom number of the main chain" is counted such that the number of atoms in the main chain will be minimum. The "main chain" consists of 1 to 3 atoms selected from a carbon atom and a hetero atom (e.g., an oxygen atom, a sulfur atom, a nitrogen atom and the like), and may be saturated or unsaturated. Sulfur atom may be oxidized.

As specific examples of the "spacer having 1 to 3 atoms in the main chain", an optionally substituted linear $C_{1-3}$ alkylene group, —$W^3$—N($R^4$)—$W^2$—, —$W^3$—O—$W^2$— or —$W^3$—S—$W^2$— wherein $W^2$ and $W^3$ are the same or different and each is a bond or an optionally substituted linear $C_{1-2}$ alkylene group, and when both of $W^2$ and $W^3$ are optionally substituted linear $C_{1-2}$ alkylene groups, then the total carbon number of the linear $C_{1-2}$ alkylene groups constituting $W^2$ and $W^3$ should be 2, and $R^4$ is a hydrogen atom or a substituent.

As the "linear $C_{1-3}$ alkylene group" of the aforementioned "optionally substituted linear $C_{1-3}$ alkylene group", —$CH_2$—, —$CH_2CH_2$— and —$CH_2CH_2CH_2$— can be mentioned.

As the "linear $C_{1-2}$ alkylene group" of the aforementioned "optionally substituted linear $C_{1-2}$ alkylene group" for $W^2$ or $W^3$, —$CH_2$— and —$CH_2CH_2$— can be mentioned.

As the aforementioned "substituent" for $R^4$, those exemplified as the "substituent" of the aforementioned "optionally substituted amino group" for $R^3$ can be mentioned, preferably, a $C_{1-6}$ alkyl group (preferably propyl, isopentyl) and the like can be mentioned.

The "spacer having 1 to 3 atoms in the main chain" for V is preferably
—$W^3$—N($R^4$)—$W^2$— [preferably —N($R^4$)$CH_2$—, and $R^4$ is a hydrogen atom, a $C_{1-6}$ alkyl group and the like];
—$W^3$—O—$W^2$— (preferably —O—);
and the like, more preferably —O—, —N($R^4$)$CH_2$— ($R^4$ is a $C_{1-6}$ alkyl group and the like) and the like.

The "$C_{1-3}$ alkylene group" and "$C_{1-2}$ alkylene group" of the aforementioned "optionally substituted $C_{1-3}$ alkylene group" and "optionally substituted $C_{1-2}$ alkylene group" optionally have 1 to 3 substituents at the substitutable positions. As such substituents, those exemplified as the "substituents" which the $C_{3-10}$ cycloalkyl group and the like exemplified as the "substituent" of the "optionally substituted hydroxy group" for $R^3$ optionally have, can be mentioned. When the number of the substituents is 2 or more, respective substituents may be the same or different.

V is preferably
(1) a bond;
(2) —$W^3$—N($R^4$)—$W^2$— [preferably —N($R^4$)$CH_2$—, and $R^4$ is a hydrogen atom, a $C_{1-6}$ alkyl group and the like];
(3) —$W^3$—O—$W^2$— (preferably —O—); and the like.

When ring A is an optionally substituted aromatic hydrocarbon group (preferably phenyl), V is preferably a bond.

When ring A is an optionally substituted aromatic heterocyclic group (preferably thiazolyl), V is preferably —N(R$^4$)CH$_2$—, and R$^4$ is a C$_{1-6}$ alkyl group.

W is an optionally substituted C$_{1-6}$ alkylene group. As the "C$_{1-6}$ alkylene group" of the "optionally substituted C$_{1-6}$ alkylene group" for W, for example, —CH$_2$—, —(CH$_2$)$_2$—, —(CH$_2$)$_3$—, —(CH$_2$)$_4$—, —(CH$_2$)$_5$—, —(CH$_2$)$_6$—, —CH(CH$_3$)—, —C(CH$_3$)$_2$—, —CH(C$_2$H$_5$)—, —CH (C$_3$H$_7$)—, —CH(CH(CH$_3$)$_2$)—, —(CH(CH$_3$))$_2$—, —(CH$_2$)$_2$C(CH$_3$)$_2$—, —(CH$_2$)$_3$C(CH$_3$)$_2$— and the like can be mentioned.

The "C$_{1-6}$ alkylene group" of the "optionally substituted C$_{1-6}$ alkylene group" for W is preferably —CH$_2$—.

The "C$_{1-6}$ alkylene group" of the "optionally substituted C$_{1-6}$ alkylene group" for W optionally has 1 to 3 substituents at the substitutable positions. As such substituents, those exemplified as the "substituents" which the C$_{3-10}$ cycloalkyl group and the like exemplified as the "substituent" of the "optionally substituted hydroxy group" for R$^3$ optionally have, can be mentioned.

W is preferably a C$_{1-6}$ alkylene group, more preferably —CH$_2$— and the like.

X is O or S.

X is preferably O.

As the preferable examples of compound (I), the following compound can be mentioned.

[Compound A]

Compound (I) wherein ring A is an optionally substituted aromatic hydrocarbon group (preferably phenyl) or an optionally substituted aromatic heterocyclic group (preferably thiazolyl) [preferably an aromatic hydrocarbon group (preferably phenyl) or an aromatic heterocyclic group (preferably thiazolyl), each of which is optionally substituted by 1 to 3 substituents selected from (1) a C$_{1-6}$ alkyl group;
(2) a C$_{1-6}$ alkoxy group optionally substituted by 1 to 3 substituents selected from
   (a) a C$_{1-6}$ alkoxy group, and
   (b) a non-aromatic heterocyclic group (e.g., oxetanyl) optionally substituted by C$_{1-6}$ alkyl group(s);
(3) a non-aromatic heterocyclyloxy group (e.g., tetrahydrothiopyranyloxy, 1-oxidotetrahydrothiopyranyloxy, 1,1-dioxidotetrahydrothiopyranyloxy); and
(4) a C$_{6-14}$ aryl group (e.g., phenyl, naphthyl) optionally substituted by C$_{1-6}$ alkyl group(s) optionally substituted by 1 to 3 halogen atoms];

ring B is an aromatic hydrocarbon (preferably benzene);

V is (1) a bond;
(2) —W$^3$—N(R$^4$)—W$^2$— [preferably —N(R$^4$)CH$_2$—, and R$^4$ is a hydrogen atom or a C$_{1-6}$ alkyl group]; or
(3) —W$^3$—O—W$^2$— (preferably —O—);
   wherein
   W$^2$ and W$^3$ are the same or different and each is a bond or an optionally substituted linear C$_{1-2}$ alkylene group, and when both of W$^2$ and W$^3$ are optionally substituted linear C$_{1-2}$ alkylene groups, then the total carbon number of the linear C$_{1-2}$ alkylene groups constituting W$^2$ and W$^3$ should be 2, and R$^4$ is a hydrogen atom or a substituent;

W is a C$_{1-6}$ alkylene group (preferably —CH$_2$—):

X is O;

R$^1$ and R$^2$ are each a hydrogen atom or a halogen atom (preferably fluorine atom); and R$^3$ is an optionally substituted hydroxy group (preferably a hydroxy group, a C$_{1-10}$ alkoxy group).

[Compound B]

Of the aforementioned [compound A], compound (I) wherein ring A is phenyl substituted by 2 or 3 (preferably 3) substituents selected from (1) a C$_{1-6}$ alkyl group;
(2) a C$_{1-6}$ alkoxy group optionally substituted by 1 to 3 substituents selected from
   (a) a C$_{1-6}$ alkoxy group, and
   (b) a non-aromatic heterocyclic group (e.g., oxetanyl) optionally substituted by C$_{1-6}$ alkyl group(s); and
(3) a non-aromatic heterocyclyloxy group (e.g., tetrahydrothiopyranyloxy, 1-oxidotetrahydrothiopyranyloxy, 1,1-dioxidotetrahydrothiopyranyloxy).

[Compound C]

Compound (I) which is selected from 2-(4-{[4'-(2-ethoxyethoxy)-2',6'-dimethylbiphenyl-3-yl]methoxy}phenyl)cyclopropanecarboxylic acid (Example 2, 3), 2-[4-({4'-[(1,1-dioxidotetrahydro-2H-thiopyran-4-yl)oxy]-2',6'-dimethylbiphenyl-3-yl}methoxy)phenyl]cyclopropanecarboxylic acid (Example 5), 2-[4-({2',6'-dimethyl-4'-[(3-methyloxetan-3-yl)methoxy]biphenyl-3-yl}methoxy)phenyl]cyclopropanecarboxylic acid (Example 7), 2-[4-({4-[((3-methylbutyl){4-[4-(trifluoromethyl)phenyl]-1,3-thiazol-2-yl}amino)methyl]benzyl}oxy)phenyl]cyclopropanecarboxylic acid (Example 9), 2-[4-({4-[(propyl{4-(4-(trifluoromethyl)phenyl]-1,3-thiazol-2-yl}amino)methyl]benzyl}oxy)phenyl]cyclopropanecarboxylic acid (Example 11), and salts thereof.

When compound (I) is in the form of a salt, the salt include metal salts, ammonium salts, salts with organic bases, salts with inorganic acids, salts with organic acids, salts with basic amino acids, salts with acidic amino acids and the like.

Preferable examples of the metal salt include alkali metal salts such as sodium salt, potassium salt and the like; alkaline earth metal salts such as calcium salt, magnesium salt, barium salt and the like; aluminum salt and the like.

Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like.

Preferable examples of the salt with inorganic acid include a salt with hydrochloric acid, hydrobromic acid, nitric acid, sulfuric acid, phosphoric acid and the like.

Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include a salt with arginine, lysine, ornithine and the like.

Preferable examples of the salt with acidic amino acid include a salt with aspartic acid, glutamic acid and the like.

Of these, a pharmacologically acceptable salt is preferable.

A prodrug of compound (I) is a compound that is converted to compound (I) due to the reaction by enzyme, gastric acid and the like under the physiological conditions in the body; that is, a compound that converts to compound (I) by enzymatic oxidation, reduction, hydrolysis and the like, and a compound that converts to compound (I) by hydrolysis and the like by gastric acid and the like.

Examples of the prodrug of compound (I) include a compound wherein an amino group of compound (I) is acylated, alkylated or phosphorylated (e.g., a compound where an amino group of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated); a compound wherein a hydroxy group of compound (I) is acylated, alkylated, phosphorylated or borated (e.g., a compound where a hydroxy group of compound (I) is acetylated, palmitoylated, propanoylated, pivaloylated, succinylated, fumarylated, alanylated or dimethylaminomethylcarbonylated); a compound wherein a carboxyl group of compound (I) is esterified or amidated (e.g., a compound where a carboxyl group of compound (I) is $C_{1-6}$ alkyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified or methylamidated) and the like. Of these, a compound wherein a carboxyl group of compound (I) is esterified by $C_{1-6}$ alkyl group such as methyl, ethyl, tert-butyl and the like is preferable. These compounds can be produced from compound (I) by a method known per se. A prodrug of compound (I) may be a compound that converts to compound (I) under physiological conditions as described in Development of Pharmaceutical Products, vol. 7, Molecule Design, pp. 163-198, Hirokawa Shoten (1990).

Hereinafter the production methods of compound (I) are explained.

Also note that a compound wherein X is NH in the formula (I) and a salt thereof can be produced in the same manner as in compound (I). In the following Scheme 2 and Scheme 3, the production method of the compound wherein X is NH in the formula (I) and a salt thereof is also explained. Specific preferable examples of the compound wherein X is NH in the formula (I) include, a compound X is replaced by NH in the aforementioned [compound B] and the like.

Each symbol of the compounds in the following Schemes is as defined above unless particularly described. Each compound described in the Schemes may form a salt as long as it does not inhibit the reactions, and as such salt, those similar to the salts of compound (I) can be mentioned.

The compound obtained in each of the following steps can also be used as a crude product in the form of a reaction mixture in the next reaction, or can be isolated from the reaction mixture according to a conventional method, and further purified easily by a separation method such as recrystallization, distillation, chromatography and the like.

Compound (I) (e.g., compounds represented by the following formulas (Ia) or (Ia') (to be abbreviated as compound (Ia) and compound (Ia'), respectively)) can be produced, for example, according to the method shown in the following Scheme 1 or a method analogous thereto.

Reaction Scheme 1

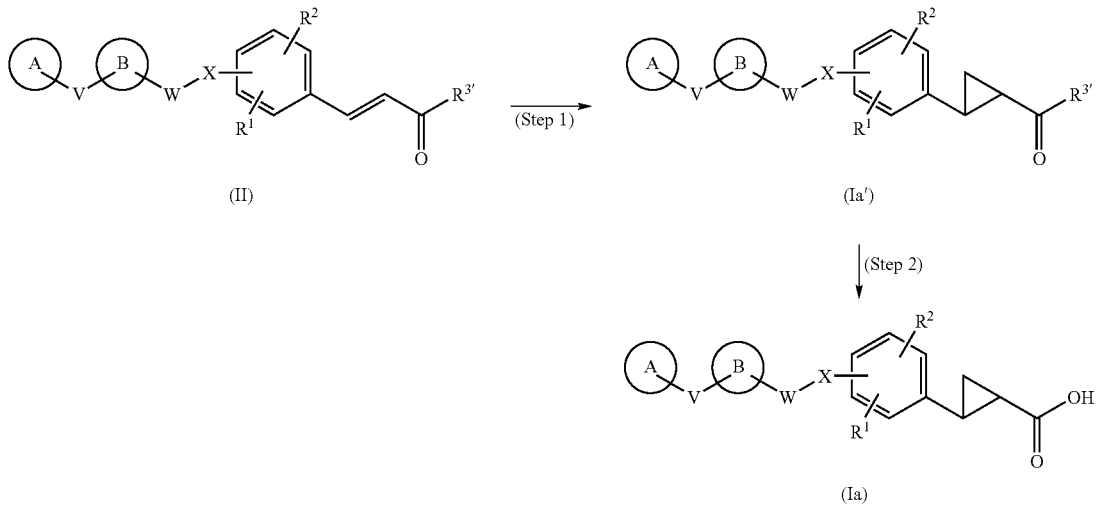

wherein $R^{3'}$ is an optionally substituted $C_{1-6}$ alkoxy group, and the other symbols are as defined above.

As the substituent of the "optionally substituted $C_{1-6}$ alkoxy group" for $R^{3'}$, those exemplified as the "substituents" which the $C_{1-10}$ alkyl group and the like exemplified as the "substituent" of the "optionally substituted hydroxy group" for $R^3$ optionally have, can be mentioned.

<Step 1>

Compound (Ia') can be produced by subjecting a compound represented by the formula (II) (to be abbreviated as compound (II)) to a cyclopropanation reaction.

The reaction can be carried out according to a method known per se, for example, the methods described in the 3rd edition, JIKKEN KAGAKU KOUZA, vol. 14, pages 91-93 (ed. Chemical Society of Japan); the 4th edition, JIKKEN KAGAKU KOUZA, vol. 25, pages 76-77 (ed. Chemical Society of Japan); Tetrahedron Lett., vol. 9, pages 629-632, 1975 and the like, or a method analogous thereto.

<Step 2>

Compound (Ia) can be produced by subjecting compound (Ia') to hydrolysis.

The hydrolysis can be carried out using an acid or a base, according to a conventional method.

As the acid, for example, inorganic acids such as hydrochloric acid, sulfuric acid and the like; Lewis acids such as boron trichloride, boron tribromide and the like; organic acids such as trifluoroacetic acid, p-toluenesulfonic acid and the like, and the like can be mentioned. The Lewis acid can be used together with a thiol or a sulfide.

As the base, for example, alkali metal hydroxides such as lithium hydroxide, sodium hydroxide, potassium hydroxide and the like; alkaline earth metal hydroxides such as barium hydroxide and the like; alkali metal carbonates such as sodium carbonate, potassium carbonate and the like; alkali metal alkoxides having 1 to 6 carbon atoms such as sodium methoxide, sodium ethoxide, potassium tert-butoxide and the like; organic bases (including hydrate) such as triethylamine, imidazole, formamidine and the like, and the like can be mentioned.

The amount of the acid or base to be used is generally about 0.5 to about 10 mol, preferably about 0.5 to about 6 mol, per 1 mol of compound (Ia').

The hydrolysis is carried out without a solvent or in a solvent inert to the reaction. As such solvent, while the solvent is not particularly limited as long as the reaction proceeds, for example, alcohols such as methanol, ethanol, propanol and the like; aromatic hydrocarbons such as benzene, toluene and the like; saturated hydrocarbons such as cyclohexane, hexane and the like; organic acids such as formic acid, acetic acid and the like; ethers such as tetrahydrofuran, 1,4-dioxane, 1,2-dimethoxyethane and the like; amides such as N,N-dimethylformamide, N,N-dimethylacetamide and the like; halogenated hydrocarbons such as dichloromethane, chloroform, carbon tetrachloride, 1,2-dichloroethane and the like; nitriles such as acetonitrile, propionitrile and the like; ketones such as acetone, methyl ethyl ketone and the like; sulfoxides such as dimethylsulfoxide and the like; water, mixed solvents thereof and the like are preferable.

The reaction time is generally 10 min to 100 hr, preferably 10 min to 24 hr. The reaction temperature is generally -10 to 200° C., preferably 0 to 120° C.

As shown in the following Scheme 2, compound (Ia') and compound (II) can be produced by reacting a compound represented by the formula (III) or the formula (IV) (to be abbreviated as compound (III) and compound (IV), respectively) with a compound represented by the formula (V) or the formula (VI) (to be abbreviated as compound (V) and compound (VI), respectively).

wherein L is a leaving group or a hydroxy group, $X^1$ is O, S or NH, $W^1$ is a bond or a $C_{1-5}$ alkylene group, R is a hydrogen atom or a $C_{1-5}$ alkyl group, and the other symbols are as defined above.

As the "leaving group" for L, for example, a halogen atom, an optionally halogenated $C_{1-6}$ alkylsulfonyloxy group (e.g., methanesulfonyloxy, ethanesulfonyloxy, trichloromethanesulfonyloxy, trifluoromethanesulfonyloxy), a $C_{6-10}$ arylsulfonyloxy group optionally having substituent(s) [for example, a $C_{6-10}$ arylsulfonyloxy group (e.g., phenylsulfonyloxy, naphthylsulfonyloxy) optionally having 1 to 3 substituents selected from a $C_{1-6}$ alkyl group, a $C_{1-6}$ alkoxy group and a nitro group and the like; specific examples include phenylsulfonyloxy group, m-nitrophenylsulfonyloxy group, p-toluenesulfonyloxy group and the like], an acyloxy group (e.g., trichloroacetoxy, trifluoroacetoxy) and the like can be mentioned.

As the "$C_{1-5}$ alkylene group" for $W^1$, a group having 1 to 5 carbon atoms, from among those exemplified as the "$C_{1-6}$ alkylene group" of the "optionally substituted $C_{1-6}$ alkylene group", can be mentioned.

As the "$C_{1-5}$ alkyl group" for R, for example, methyl, ethyl, propyl, isopropyl, butyl, isobutyl, sec-butyl, tert-butyl, pentyl, isopentyl, neopentyl and the like can be mentioned.

<Step 3>

(i) when $X^1$ is O or S, and L is a hydroxy group, compound (Ia') and compound (II) can be produced by subjecting compound (III) or compound (IV) and compound (V) to the Mitsunobu reaction (e.g., Synthesis, pages 1-27, 1981).

In the Mitsunobu reaction, compound (III) or compound (IV) reacted with compound (V) in the presence of an azodicarbonyl compound (e.g., diethyl azodicarboxylate, diisopropyl azodicarboxylate, 1,1'-(azodicarbonyl)dipiperidine) and a phosphine (e.g., triphenylphosphine, tributylphosphine).

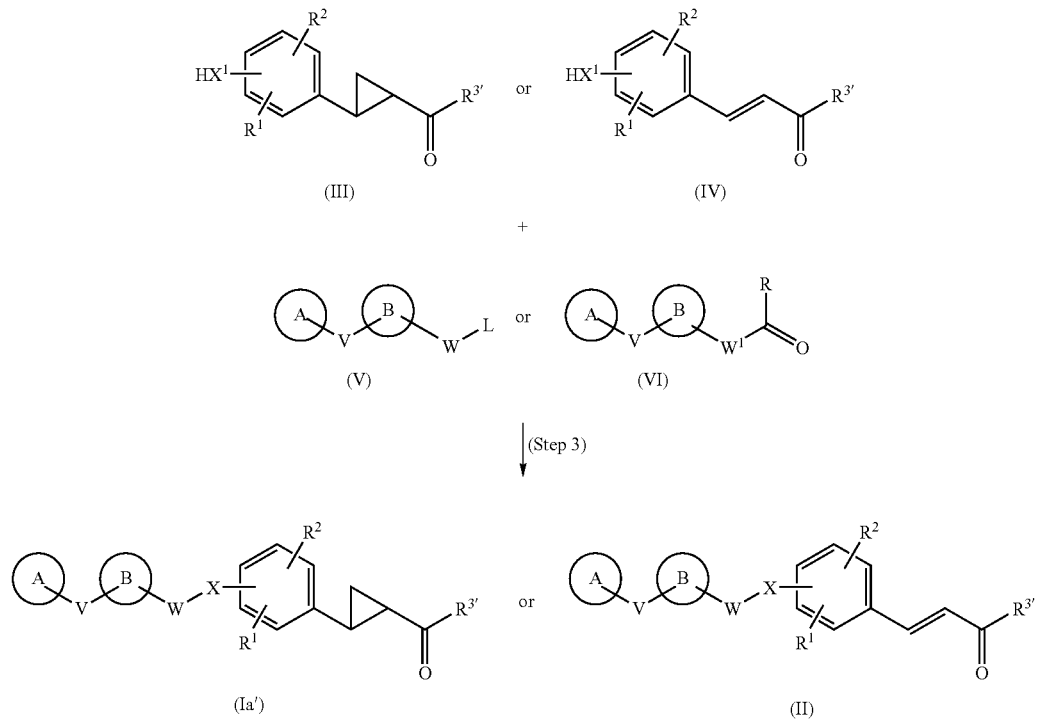

The amount of compound (V) to be used is generally about 1 to about 5 mol, preferably about 1 to about 2 mol, per 1 mol of compound (III) or (IV).

The amount of the azodicarbonyl compound and phosphine to be used is generally about 1 to about 5 mol, preferably about 1 to about 2 mol, per 1 mol of compound (III) or compound (IV), respectively.

The reaction is advantageously carried out in a solvent inert to the reaction. As such solvent, while the solvent is not particularly limited as long as the reaction proceeds, for example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; halogenated hydrocarbons such as dichloromethane, chloroform, carbon tetrachloride, 1,2-dichloroethane and the like; nitriles such as acetonitrile, propionitrile and the like; ketones such as acetone, ethylmethylketone and the like; sulfoxides such as dimethylsulfoxide and the like, mixed solvents thereof and the like are preferable.

The reaction time is generally 5 min to 100 hr, preferably 30 min to 72 hr. The reaction temperature is generally -20 to 200° C., preferably 0 to 100° C. (ii) when $X^1$ is O, S or NH, and L is a leaving group, compound (Ia') and compound (II) can be produced by reacting compound (III) or compound (IV) with compound (V) in the presence of a base.

As the base, for example, alkali metal hydroxides such as lithium hydroxide, sodium hydroxide, potassium hydroxide and the like; alkaline earth metal hydroxides such as barium hydroxide and the like; alkali metal carbonates such as sodium carbonate, potassium carbonate, cesium carbonate and the like; alkali metal hydrogencarbonates such as sodium hydrogencarbonate and the like; acetates such as sodium acetate, ammonium acetate and the like; aromatic amines such as pyridine, lutidine and the like; tertiary amines such as triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine, N-methylmorpholine and the like; alkali metal hydrides such as sodium hydride, potassium hydride and the like; metal amides such as sodium amide, lithium diisopropylamide, lithium hexamethyldisilazide and the like; alkali metal alkoxides having 1 to 6 carbon atoms such as sodium methoxide, sodium ethoxide, sodium tert-butoxide, potassium tert-butoxide and the like; organic lithiums such as methyllithium, n-butyllithium, sec-butyllithium, tert-butyllithium and the like, and the like can be mentioned.

The amount of compound (V) to be used is generally about 0.8 to about 10 mol, preferably about 0.9 to about 2 mol, per 1 mol of compound (III) or compound (IV).

The amount of the base to be used is generally about 1 to about 10 mol, preferably about 1 to about 3 mol, per 1 mol of compound (III) or compound (IV).

The reaction is advantageously carried out in a solvent inert to the reaction. As the solvent, those exemplified in (i) of Step 3 can be mentioned.

The reaction time is generally 10 min to 12 hr, is preferably 20 min to 6 hr. The reaction temperature is generally −70 to 150° C., preferably −20 to 100° C. (iii) when $X^1$ is NH, compound (Ia') and compound (II) can also be produced by subjecting compound (III) or compound (IV) with compound (VI) to a reductive amination reaction (e.g., described in JIKKEN KAGAKU KOUZA, 4th Edition., vol. 20, pp. 282-284 and 366-368 (Chemical Society of Japan); J. Am. Chem. Soc., vol. 93, pp. 2897-2904, 1971; Synthesis, pp. 135, 1975 and the like), besides the above-mentioned (ii).

In the reductive amination reaction, compound (Ia') and compound (II) can be obtained by subjecting an imine which is produced by the dehydrating reaction of compound (III) or compound (IV) with compound (VI), to a reduction reaction.

The dehydrating reaction is accelerated by adding a dehydrating agent such as molecular sieve and the like, or a catalyst such as zinc chloride, phosphoryl chloride, boron trifluoride, titanium tetrachloride and the like to the system.

The reduction reaction is generally carried out using a reducing agent according to a conventional method. As the reducing agent, for example, metal hydrides such as aluminum hydride, diisobutylaluminum hydride, tributyltin hydride and the like; metallic hydride complex compounds such as sodium cyanoborohydride, sodium triacetoxyborohydride, sodium borohydride, lithium aluminum hydride and the like; borane complexes such as borane tetrahydrofuran complex, borane dimethyl sulfide complex and the like; alkylboranes such as thexylborane, disiamylborane and the like; diborane; metals such as zinc, aluminum, tin, iron and the like; alkali metals such as sodium, lithium and the like/liquid ammonia (Birch reduction) and the like can be mentioned.

The amount of the reducing agent to be used is appropriately determined according to the kind of the reducing agent. For example, the amount of each of the metal hydride, metal hydrogen complex compound, borane complex, alkylboranes and diborane to be used is generally about 0.25 to about 10 mol, preferably about 0.5 to about 5 mol, per 1 mol of compound (III) or compound (IV), and the amount of the metals (including alkali metal used for Birch reduction) to be used is generally about 1 to about 20 mol, preferably about 1 to about 5 mol, per 1 mol of compound (III) or compound (IV).

The reduction reaction can also be carried out by a hydrogenation reaction. In this case, for example, catalysts such as palladium carbon, palladium black, platinum dioxide, Raney-nickel, Raney-cobalt and the like are used. The amount of the catalyst to be used is generally about 5 to about 1000 wt %, preferably about 10 to about 300 wt %, per 1 mol of compound (III) or compound (IV).

The hydrogenation reaction can also be carried out using various hydrogen sources instead of gaseous hydrogen. As such hydrogen sources, for example, formic acid, ammonium formate, triethylammonium formate, sodium phosphinate, hydrazine and the like can be mentioned. The amount of the hydrogen source to be used is generally about 1 to about 10 mol, preferably about 1 to about 5 mol, per 1 mol of compound (III) or compound (IV).

This reaction is advantageously carried out using a solvent inert to the reaction. While the solvent is not particularly limited as long as the reaction proceeds, for example, alcohols such as methanol, ethanol, 1-propanol, 2-propanol, tert-butyl alcohol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoric triamide and the like; organic acids such as formic acid, acetic acid, propanoic acid, trifluoroacetic acid, methanesulfonic acid and the like, a mixed solvent thereof and the like are preferable.

The amount of compound (VI) to be used is generally about 0.5 to about 5 mol, preferably about 1 to about 2 mol, per 1 mol of compound (III) or compound (IV).

While the reaction time varies depending on the reagent and solvent to be used, it is generally 10 min to 100 hr, preferably 30 min to 50 hr. The reaction temperature is generally −20 to 100° C., preferably 0 to 80° C.

Compounds (III), (IV), (V) and (VI) to be used in the aforementioned Scheme 2 can be easily obtained as a commercially available product, or can also be produced according to a method known per se.

Compound (III) can be produced, for example, according to a method shown in the following Scheme 3, or a method analogous thereto.

Reaction Scheme 3

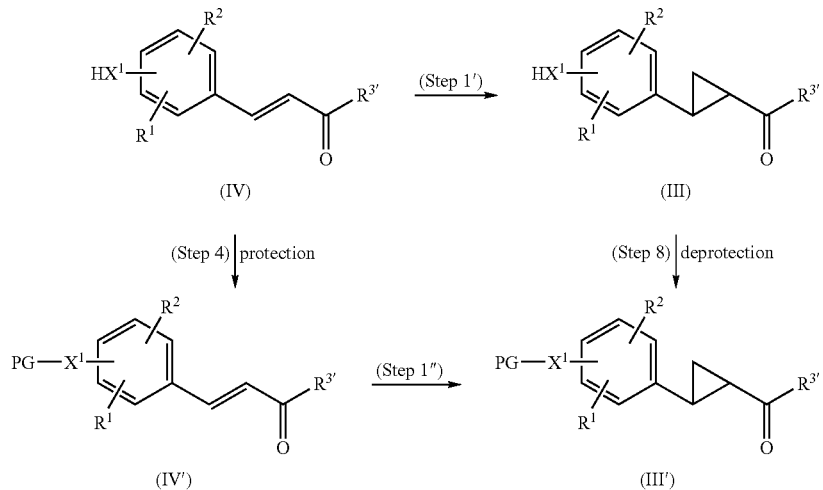

wherein PG is a protecting group, and the other symbols are as defined above.

As the "protecting group" for PG, the below-mentioned hydroxy-protecting group, amino-protecting group, mercapto-protecting group and the like can be mentioned.

<Step 1'>

Compound (III) can be produced by subjecting compound (IV) to a cyclopropanation reaction.

The cyclopropanation reaction can be carried out in the same manner as in Step 1 of the above-mentioned Scheme 1, or according to a method analogous thereto.

<Step 4>

A compound represented by the formula (IV') (to be abbreviated as compound (IV')) can be produced by subjecting compound (IV) to a protecting group-introducing reaction known per se, which is used in the peptide chemistry, or a reaction analogous thereto.

Step 1''>

A compound represented by the formula (III') (to be abbreviated as compound (III')) can be produced by subjecting compound (IV') to a cyclopropanation reaction.

The cyclopropanation reaction can be carried out in the same manner as in Step 1 of the above-mentioned Scheme 1, or according to a method analogous thereto.

<Step 5>

Compound (III) can be produced by subjecting compound (III') to a deprotection reaction known per se, which is used in the peptide chemistry, or a reaction analogous thereto.

Of compound (V) and compound (VI), Compound (V') and compound (VI') wherein V is $V^1$ ($V^1$ is a bond, an optionally substituted linear $C_{1-3}$ alkylene group, —$W^3$—N($R^4$)—$W^2$—, —$W^3$—O—$W^2$— or —$W^3$—S—$W^2$—, and $W^2$, $W^3$ and $R^4$ are as defined above) can be produced, for example, according to a method shown in the following Scheme 4 or a method analogous thereto.

Reaction Scheme 4

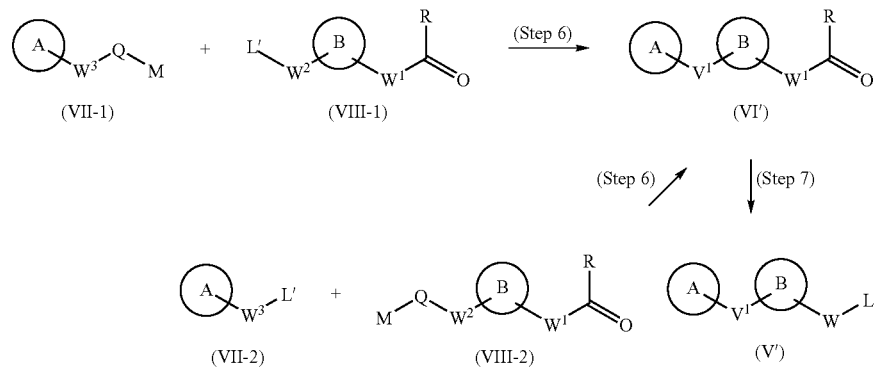

wherein Q is —N(R^A)—, —O— or —S—, M is a hydrogen atom or a metal, L' is a leaving group, and the other symbols are as defined above.

As the "leaving group" for L', those exemplified as the aforementioned L can be mentioned.

As the "metal" for M, for example, potassium, sodium, lithium, magnesium, copper, mercury, zinc, thallium, boron, tin and the like can be mentioned, and these may be complexed.

<Step 6>

Compound (VI') can be produced by, (i) reacting compound (VII-1) with compound (VIII-1), or (ii) reacting compound (VII-2) with compound (VIII-2). Hereinafter, unless otherwise specified, compound (VII-1) and compound (VII-2) are collectively referred to as compound (VII) and, unless otherwise specified, compound (VIII-1) and compound (VIII-2) are collectively referred to as compound (VIII).

The reaction of compound (VII) with compound (VIII) is generally carried out in the presence of a base. As the base, for example, alkali metal hydrides such as sodium hydride, potassium hydride and the like; alkali metal hydroxides such as lithium hydroxide, sodium hydroxide, potassium hydroxide and the like; alkaline earth metal hydroxide such as magnesium hydroxide, calcium hydroxide and the like; alkali metal carbonate such as sodium carbonate, potassium carbonate and the like; alkali metal hydrogencarbonates such as sodium hydrogencarbonate, potassium hydrogencarbonate and the like; alkali metal alkoxides having 1 to 6 carbon atoms such as sodium methoxide, sodium ethoxide, sodium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; organic lithiums such as methyllithium, n-butyllithium, sec-butyllithium, tert-butyllithium and the like; metal amides such as sodium amide, lithium diisopropylamide, lithiumhexamethyl disilazide and the like, and the like can be mentioned.

The amount of compound (VIII) to be used is generally about 0.1 to about 10 mol, preferably about 0.5 to about 2 mol, per 1 mol of compound (VII). The amount of base to be used is generally about 1 to about 20 mol, preferably about 1 to about 5 mol, per 1 mol of compound (VII).

The reaction of compound (VII) with compound (VIII) is advantageously carried out in a solvent inert to the reaction. As such solvent, while the solvent is not particularly limited as long as the reaction proceeds, for example, alcohols such as methanol, ethanol, propanol, isopropanol, butanol, tert-butanol and the like; ethers such as 1,4-dioxane, tetrahydrofuran, diethyl ether, tert-butyl methyl ether, diisopropyl ether, 1,2-dimethoxyethane and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as N,N-dimethylformamide, N,N-dimethylacetamide and the like; nitriles such as acetonitrile, propionitrile and the like; sulfoxides such as dimethylsulfoxide and the like; sulforane; hexamethylphosphoramide; water, mixed solvents thereof and the like are preferable.

The reaction of compound (VII) with compound (VIII) can be accelerated using a metal catalyst in some cases. As the metal catalyst, metal complexes having various ligands can be mentioned, for example, palladium compounds [e.g.: palladium(II) acetate, tetrakis(triphenylphosphine)palladium(0), bis(triphenylphosphine)palladium(II) chloride, dichlorobis(triethylphosphine)palladium(II), tris(dibenzylideneacetone)dipalladium-2,2'-bis(diphenylphosphino)-1,1'-binaphthyl, complex of palladium(II) acetate and 1,1'-bis(diphenylphosphino)ferrocene]; nickel compounds [e.g.: tetrakis(triphenylphosphine)nickel(0), bis(triethylphosphine)nickel(II) chloride, bis(triphenylphosphine)nickel(II) chloride]; rhodium compounds [e.g.: tris(triphenylphosphine)rhodium(III) chloride]; cobalt compounds; copper compounds [e.g.: copper oxide, copper(II) chloride]; platinum compounds and the like can be mentioned.

Of these, palladium compounds, nickel compounds and copper compounds are preferable. The amount of the metal catalyst to be used is generally about 0.000001 to about 5 mol, preferably about 0.0001 to about 1 mol, per 1 mol of compound (XIII). When a metal catalyst unstable for oxygen is used in this reaction, the reaction is preferably carried out under an inert gas (e.g., argon gas or nitrogen gas) stream.

The reaction temperature is generally -10 to 250° C., preferably 0 to 150° C. While the reaction time varies depending on the kind of compound (VII), compound (VIII), the metal catalyst, base or solvent to be used, the reaction temperature and the like, it is generally 1 min to 200 hr, preferably 5 min to 100 hr.

<Step 7>

Compound (V') can be produced from compound (VI'). Compound (V') wherein L is a hydroxy group can be produced by subjecting compound (VI') to a reduction reaction. The reduction reaction is carried out in the same manner as in the reduction reaction using a reducing agent, which is exemplified as Step 3 of the above-mentioned Scheme 2. As the reducing agent, sodium borohydride, diisobutylaluminum hydride, lithium aluminum hydride and the like are preferable.

Compound (V') wherein L is a leaving group can be produced by reacting compound (V') wherein L is a hydroxy group (hereinafter sometimes to be abbreviated as compound (V'')) with a halogenating agent or a sulfonylating agent.

As the halogenating agent, for example, thionyl chloride, phosphorus tribromide and the like can be used. In this case, compound (V') wherein L is a halogen atom (e.g., chlorine, bromine) can be produced.

The reaction of compound (V'') with a halogenating agent is generally carried out in a solvent that does not adversely influence the reaction. As the solvent that does not adversely influence the reaction, for example, halogenated hydrocarbons such as dichloromethane, chloroform, carbon tetrachloride and the like; aromatic hydrocarbons such as benzene, toluene, xylene and the like; ethers such as diethyl ether, diisopropyl ether, tert-butyl methyl ether, tetrahydrofuran, 1,4-dioxane, 1,2-dimethoxyethane and the like; esters such as methyl acetate, ethyl acetate, n-butyl acetate, tert-butyl acetate and the like, and the like can be mentioned. Alternatively, an excess amount of the halogenating agent may be used as a solvent.

The amount of the halogenating agent to be used is generally about 1 to about 10 mol, preferably about 1 to about 5 mol, per 1 mol of compound (V'').

The reaction temperature is generally −20 to 100° C. The reaction time is generally 0.5 to 24 hr.

As the sulfonylating agent, for example, sulfonyl halides such as methanesulfonyl chloride, benzenesulfonyl chloride, p-toluenesulfonyl chloride and the like; sulfonic acid anhydrides such as methanesulfonic anhydride, trifluoromethanesulfonic anhydride and the like, and the like can be used. In this case, compound (V') wherein L is, for example, methanesulfonyloxy, trifluoromethanesulfonyloxy, benzenesulfonyloxy, p-toluenesulfonyloxy and the like can be produced.

The reaction of compound (V") with a sulfonylating agent is generally carried out in a solvent that does not adversely influence the reaction in the presence of a base. As the solvent that does not adversely influence the reaction, for example, halogenated hydrocarbons such as dichloromethane, chloroform, carbon tetrachloride and the like; aromatic hydrocarbons such as benzene, toluene, xylene and the like; ethers such as diethyl ether, diisopropyl ether, tert-butyl methyl ether, tetrahydrofuran, 1,4-dioxane, 1,2-dimethoxyethane and the like; esters such as methyl acetate, ethyl acetate, n-butyl acetate, tert-butyl acetate and the like, and the like can be mentioned.

The amount of the sulfonylating agent to be used is generally about 1 to about 10 mol, preferably about 1 to about 5 mol, per 1 mol of compound (V").

As the base, for example, amines such as triethylamine, N-methylmorpholine and the like; alkali metal salts such as sodium hydrogencarbonate, potassium hydrogencarbonate, potassium carbonate and the like, and the like can be mentioned.

The amount of the base to be used is generally about 1 to about 10 mol, preferably about 1 to about 5 mol, per 1 mol of compound (V").

The reaction temperature is generally −20 to 100° C. The reaction time is generally 0.5 to 24 hr.

In each of the above-mentioned reaction steps, compound (I) can also be produced by performing, when desired, each of known hydrolysis reaction, deprotection reaction, acylation reaction, alkylation reaction, hydrogen addition reaction, oxidation reaction, reduction reaction, carbon chain extension reaction and substituent exchange reaction independently, or two or more thereof in combination. These reactions can be performed, for example, according to the method described in JIKKEN KAGAKU KOUZA, vol. 14, vol. 15, (ed. Chemical Society of Japan) and the like.

In addition, in each of the aforementioned reactions, when the starting compound has an amino group, a carboxyl group, a hydroxy group or a mercapto group as a substituent, a protecting group generally used in peptide chemistry and the like may be introduced into these groups. By removing the protecting group as necessary after the reaction, the objective compound can be obtained.

As the amino-protecting group, for example, formyl group; $C_{1-6}$ alkyl-carbonyl group, phenylcarbonyl group, $C_{1-6}$ alkoxy-carbonyl group, allyloxycarbonyl (Alloc) group, phenyloxycarbonyl group, fluorenylmethyloxycarbonyl (Fmoc) group, $C_{7-10}$ aralkyl-carbonyl group (e.g., benzylcarbonyl), $C_{7-10}$ aralkyloxy-carbonyl group (e.g., benzyloxycarbonyl (Z)), $C_{7-10}$ aralkyl group (e.g., benzyl), trityl group, phthaloyl group, dithiasuccinoyl group, N,N-dimethylaminomethylene group, each optionally having substituent(s), and the like can be mentioned. As these substituents, for example, phenyl group, halogen atom, $C_{1-6}$ alkyl-carbonyl group, optionally halogenated $C_{1-6}$ alkoxy group (e.g., methoxy, ethoxy, trifluoromethoxy), nitro group and the like are used. The number of the substituent(s) is about 1 to 3.

As the carboxyl-protecting group, for example, $C_{1-6}$ alkyl group, allyl group, benzyl group, phenyl group, trityl group, trialkylsilyl group (e.g., trimethylsilyl, tert-butyldimethylsilyl, diisopropylethylsilyl), each optionally having substituent(s), and the like can be mentioned. As these substituents, halogen atom, formyl group, $C_{1-6}$ alkyl-carbonyl group, optionally halogenated $C_{1-6}$ alkoxy group (e.g., methoxy, ethoxy, trifluoromethoxy), nitro group and the like are used. The number of the substituent(s) is about 1 to 3.

As the hydroxy-protecting group, for example, $C_{1-6}$ alkyl group, $C_{7-20}$ aralkyl group (e.g., benzyl, trityl), formyl group, $C_{1-6}$ alkyl-carbonyl group, benzoyl group, $C_{7-10}$ aralkyl-carbonyl group (e.g., benzylcarbonyl), 2-tetrahydropyranyl group, tetrahydrofuranyl group and trialkylsilyl group (e.g., trimethylsilyl, tert-butyldimethylsilyl, diisopropylethylsilyl), each optionally having substituent(s), and the like can be mentioned. As these substituents, halogen atom, $C_{1-6}$ alkyl group, phenyl group, $C_{7-10}$ aralkyl group (e.g., benzyl), $C_{1-6}$ alkoxy group, nitro group and the like are used. The number of the substituent(s) is about 1 to 4.

As the mercapto-protecting group, for example, $C_{1-6}$ alkyl group, $C_{7-20}$ aralkyl group (e.g., benzyl, trityl), each optionally having substituent(s), and the like can be mentioned. As these substituents, halogen atom, $C_{1-6}$ alkyl group, phenyl group, $C_{7-10}$ aralkyl group (e.g., benzyl), $C_{1-6}$ alkoxy group, $C_{1-6}$ alkyl-carbonyl group, nitro group and the like are used. The number of the substituent(s) is about 1 to 4.

For elimination of the protecting group, a method known per se or a method analogous thereto is used. For example, treatments with acid, base, reduction, ultraviolet rays, hydrazine, phenylhydrazine, sodium N-methyldithiocarbamate, tetrabutylammonium fluoride, palladium acetate and the like can be used.

compound (I) obtained in this manner, other reaction intermediates and starting compounds thereof can be isolated and purified from the reaction mixture by a method known per se, such as extraction, concentration, neutralization, filtration, distillation, recrystallization, column chromatography, thin layer chromatography, preparative high performance liquid chromatography (preparative HPLC), medium pressure preparative liquid chromatography (medium pressure preparative LC) and the like.

When compound (I) has optical isomers, these respective optical isomers and mixtures thereof are naturally encompassed in the scope of the present invention, and where desired, these isomers can also be subjected to optical resolution or individually produced according to a method known per se.

When compound (I) is present as a configurational isomer, diastereomer, conformer or the like, each can be isolated by the above-mentioned separation and purification methods on demand. In addition, when compound (I) is in the form of a racemate, it can be separated into S- and R-forms by any conventional optical resolution.

When compound (I) includes stereoisomers, both the isomers alone and mixtures of each isomers are encompassed in the scope of the present invention.

In addition, compound (I) may be a hydrate or non-hydrate.

Compound (I) may be labeled with an isotope (e.g., $^3H$, $^{14}C$, $^{35}S$) or the like.

Since compound (I) and a prodrug thereof (hereinafter a compound of the formula (I) wherein X is NH, a salt thereof and a prodrug thereof are sometimes to be also collectively abbreviated as a compound of the present invention) have a GPR40 receptor function modulating action (GPR40 receptor agonist activity and GPR40 receptor antagonist activity), particularly a GPR40 receptor agonist activity, show low toxicity and fewer side effects (e.g., acute toxicity, chronic toxicity, genetic toxicity, reproductive toxicity, cardiotoxicity, drug interaction, carcinogenicity), they are useful as safe GPR40 receptor function regulators, preferably GPR40 agonists.

Moreover, the compound of the present invention is superior in efficacy sustainability, and can exhibit a uperior GPR40 receptor function modulating action (preferably GPR40 receptor agonist activity) for a long time (e.g., 4 hr).

Moreover, the compound of the present invention is superior in pharmacokinetics (e.g., oral absorbability).

A pharmaceutical agent containing the compound of the is present invention shows a superior GPR40 receptor function modulating action in mammals (e.g., mouse, rat, hamster, rabbit, cat, dog, bovine, sheep, monkey, human etc.), and are useful as regulators of physiological function in which GPR40 receptor is involved or agents for the prophylaxis or treatment of disease state or disease in which GPR40 receptor is involved. Here, the "pathology or disease" is not limited to "a pathology or disease involving a GPR40 receptor" but also includes "a pathology or disease caused by abnormality in GPR40 receptor" and "a pathology or disease that can be improved or treated by functional regulation of GPR40 receptor".

To be specific, a pharmaceutical agent containing the compound of the present invention is useful as insulin secretion regulators (preferably insulin secretagogues), hypoglycemic agents and pancreatic β cell protectors.

Moreover, a pharmaceutical agent containing the compound of the present invention is useful as agents for the prophylaxis or treatment of diseases such as diabetes, impaired glucose tolerance, ketosis, acidosis, diabetic neuropathy, diabetic nephropathy, diabetic retinopathy, macular edema, hyperlipidemia, genital disorder, skin disease, arthropathy, osteopenia, arteriosclerosis, thrombotic disease, dyspepsia, memory and learning disorder, depression, depression and mania, schizophrenia, attention deficit hyperactivity disorder, visual disorder, appestat disorder (e.g., hyperorexia), obesity, hypoglycemia, hypertension, edema, insulin resistance, unstable diabetes, fatty atrophy, insulin allergy, insulinoma, lipotoxicity, pancreatic fatigue, hyperinsulinemia, cancers (e.g., breast cancer), metabolic syndrome, immune diseases (e.g., immunodeficiency), inflammatory disease (e.g., enteritis, arthritis, allergy), multiple sclerosis, acute kidney failure and the like; particularly, diseases such as diabetes, impaired glucose tolerance, ketosis, acidosis, diabetic neuropathy, diabetic nephropathy, diabetic retinopathy, macular edema, hyperlipidemia, genital disorder, skin disease, arthropathy, osteopenia, arteriosclerosis, thrombotic disease, dyspepsia, memory and learning disorder and the like. Here, diabetes includes type I diabetes, type II diabetes, gestational diabetes, obesity diabetes and the like. In addition, hyperlipidemia includes hypertriglyceridemia, hypercholesterolemia, hypo-high-density-lipoproteinemia, postprandial hyperlipidemia and the like.

For diagnostic criteria of diabetes, Japan Diabetes Society reported new diagnostic criteria.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) and WHO reported new diagnostic criteria of diabetes.

According to these reports, diabetes is a condition showing a fasting blood glucose level (glucose concentration of intravenous plasma) of not less than 126 mg/dl or a 75 g oral glucose tolerance test 2 h level (glucose concentration of intravenous plasma) of not less than 200 mg/dl.

According to the above-mentioned reports of ADA and WHO, impaired glucose tolerance is a condition showing a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 100 mg/dl and less than 126 mg/dl is called IFG (Impaired Fasting Glucose). On the other hand, according to the report of WHO, among the IFG (Impaired Fasting Glucose), a condition showing a fasting blood glucose level (glucose concentration of intravenous plasma) of not less than 110 mg/dl and less than 126 mg/dl is called IFG (Impaired Fasting Glycemia).

The compound of the present invention can also be used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can also prevent progress of borderline type, impaired glucose tolerance, IFG (Impaired Fasting Glucose) or IFG (Impaired Fasting Glycemia) into diabetes.

The compound of the present invention is also useful as a therapeutic agent for diabetes with sulfonylurea secondary failure and affords a superior insulin secretion effect and a hypoglycemic effect for diabetic patients for whom sulfonylurea compounds and fast-acting insulin secretagogues fail to provide an insulin secretion effect, and therefore, fail to provide a sufficient hypoglycemic effect.

As the sulfonylurea compound here, a compound having a sulfonylurea skeleton or a derivative thereof (e.g., tolbutamide, glibenclamide, gliclazide, chlorpropamide, tolazamide, acetohexamide, glyclopyramide, glimepiride, glipizide, glybuzole and the like) can be mentioned.

As the fast-acting insulin secretagogue, a compound that promotes insulin secretion from pancreatic β cell in the same manner as a sulfonylurea compound, though it does not have a sulfonylurea skeleton, for example, glinide compounds (such as repaglinide, senaglinide, nateglinide, mitiglinide, a calcium salt hydrate thereof etc.), and the like, can be mentioned.

A pharmaceutical agent containing the compound of the present invention shows low toxicity, and can be safely administered orally or parenterally (e.g., topical, rectal, intravenous administration) in the form of the compound of the present invention as it is or after admixing with a pharmacologically acceptable carrier to give a pharmaceutical preparation according to a method known per se employed for general production methods for pharmaceutical preparations.

As the dosage form of the aforementioned pharmaceutical preparation, for example, an oral agent such as tablets (inclusive of sublingual tablets and orally disintegrable tablets), capsules (inclusive of soft capsules and micro capsules), granules, powders, troches, syrups, emulsions, suspensions and the like; a parenteral agent such as injections (e.g., subcutaneous injections, intravenous injections, intramuscular injections, intraperitoneal injections, drip infusions), external agents (e.g., transdermal preparations, ointments), suppositories (e.g., rectal suppositories, vaginal suppositories), pellets, nasal preparations, pulmonary preparations (inhalations), ophthalmic preparations and the like can be mentioned.

These agents may be controlled-release preparations such as rapid-release preparations and sustained-release preparations (e.g., sustained-release microcapsules).

The content of the compound of the present invention in a pharmaceutical preparation is about 0.01 to about 100% by weight relative to the whole preparation. While the dose of the compound of the present invention varies depending on the administration subject, administration route, diseases, condition and the like, for example, the compound of the present invention can be orally administered to an adult patient with diabetes (body weight about 60 kg) in about 0.01 to about 30 mg/kg body weight per day, preferably about 0.1 to about 20 mg/kg body weight per day, more preferably about 1 to about 20 mg/kg body weight per day, which may be given at once or in several portions a day.

As the above-mentioned pharmacologically acceptable carrier, various organic or inorganic carrier substances conventionally used as a preparation material can be mentioned. For example, excipient, lubricant, binder and disintegrant for solid preparations, solvent, solubilizing agent, suspending agent, isotonicity agent, buffer and soothing agent for liquid preparations, and the like can be mentioned. Where necessary, additives such as preservative, antioxidant, colorant, sweetening agent, adsorbing agent, wetting agent and the like can also be used.

As the excipient, for example, lactose, sucrose, D-mannitol, starch, corn starch, crystalline cellulose, light anhydrous silicic acid and the like can be mentioned.

As the lubricant, for example, magnesium stearate, calcium stearate, talc, colloidal silica and the like can be mentioned.

As the binder, for example, crystalline cellulose, sucrose, D-mannitol, dextrin, hydroxypropylcellulose, hydroxypropylmethylcellulose, polyvinylpyrrolidone, starch, saccharose, gelatin, methylcellulose, carboxymethylcellulose sodium and the like can be mentioned.

As the disintegrant, for example, starch, carboxymethylcellulose, carboxymethylcellulose calcium, carboxymethylstarch sodium, L-hydroxypropylcellulose and the like can be mentioned.

As the solvent, for example, water for injection, alcohol, propylene glycol, macrogol, sesame oil, corn oil, olive oil and the like can be mentioned.

As the solubilizing agent, for example, polyethylene glycol, propylene glycol, D-mannitol, benzyl benzoate, ethanol, trisaminomethane, cholesterol, triethanolamine, sodium carbonate, sodium citrate and the like can be mentioned.

As the suspending agent, for example, surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like, and the like can be mentioned.

As the isotonicity agent, for example, glucose, D-sorbitol, sodium chloride, glycerin, D-mannitol and the like can be mentioned.

As the buffer, for example, buffers of phosphate, acetate, carbonate, citrate and the like, and the like can be mentioned.

As the soothing agent, for example, benzyl alcohol and the like can be mentioned.

As the preservative, for example, p-hydroxybenzoates, chlorobutanol, benzyl alcohol, phenethyl alcohol, dehydroacetic acid, sorbic acid and the like can be mentioned.

As the antioxidant, for example, sulfite, ascorbic acid, α-tocopherol and the like can be mentioned.

As the colorant, for example, aqueous edible tar pigments (e.g., foodcolors such as Food Color Red Nos. 2 and 3, Food Color Yellow Nos. 4 and 5, Food Color Blue Nos. 1 and 2 and the like), water insoluble lake pigments (e.g., aluminum salt of the aforementioned aqueous edible tar pigment), natural pigments (e.g., β-carotene, chlorophyll, red iron oxide) and the like can be mentioned.

As the sweetening agent, for example, saccharin sodium, dipotassium glycyrrhizinate, aspartame, stevia and the like can be mentioned.

The compound of the present invention can be used in combination with drugs such as therapeutic agents for diabetes, therapeutic agents for diabetic complications, therapeutic agents for hyperlipidemia, antihypertensive agents, antiobesity agents, diuretics, chemotherapeutic agents, immunotherapeutic agents, antiinflammatory agents, antithrombotic agents, therapeutic agents for osteoporosis, vitamins, antidementia agents, therapeutic agents for pollakiuria or urinary incontinence, therapeutic agents for dysuria and the like (hereinafter, sometimes to be abbreviated as drug X).

As the above-mentioned therapeutic agents for diabetes, insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), PPAR function modulators (e.g., pioglitazone or a salt thereof (preferably hydrochloride), rosiglitazone or a salt thereof (preferably maleate), Netoglitazone, FK-614, Rivoglitazone, Muraglitazar, compounds described in WO01/38325, Tesaglitazar, Ragaglitazar, Edaglitazone (BM-13-1258), Metaglidasen (MBX-102), Naveglitazar (LY-519818), MX-6054, Balaglitazone, LY-510929, AMG131 (T-131) or a salt thereof, THR-0921), α-glucosidase inhibitors (e.g., voglibose, acarbose, miglitol, emiglitate), biguanides (e.g., phenformin, metformin, buformin or salts thereof (e.g., hydrochloride, fumarate, succinate)), insulin secretagogues [sulfonylureas (e.g., tolbutamide, glibenclamide, gliclazide, chlorpropamide, tolazamide, acetohexamide, glyclopyramide, glimepiride), repaglinide, senaglinide, mitiglinide or calcium salt hydrate thereof, nateglinide], GLP-1 receptor agonists [e.g., GLP-1, GLP-1MR agent, NN-2211, AC-2993 (exendin-4), BIM-51077, Aib(8,35)hGLP-1(7,37)NH$_2$, CJC-1131], dipeptidyl peptidase IV inhibitors (e.g., NVP-DPP-278, PT-100, P32/98, P93/01, NVP-DPP-728, Vidagliptin (LAF237), Saxagliptin (BMS-477118), T-6666, Sitagliptin phosphate (MK-431), TS-021), 33 agonists (e.g., AJ-9677), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists), SGLT (sodium-glucose cotransporter) inhibitors (e.g., T-1095), 11β-hydroxysteroid dehydrogenase inhibitors (e.g., BVT-3498), adiponectin or agonists thereof, IKK inhibitors (e.g., AS-2868), leptin resistance improving drugs, somatostatin receptor agonists (compounds described in WO01/25228, WO03/42204, WO98/44921, WO98/45285 and WO99/22735), glucokinase activators (e.g., RO-4389620, PSN-010) and the like can be mentioned.

Examples of the therapeutic agents for diabetic complications include aldose reductase inhibitors (e.g., Tolrestat, Epalrestat, Zenarestat, Zopolrestat, Fidarestat, Ranirestat (AS-3201), Minalrestat, CT-112), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy)propyl]oxazole)), protein kinase C (PKC) inhibitors (e.g., ruboxistaurin mesylate), AGE inhibitors (e.g., ALT-945, pimagedine, N-phenacylthiazolium bromide (ALT-766), EXO-226, ALT-711, Pyridorin, Pyridoxamine), active oxygen scavengers (e.g., thioctic acid), cerebral vasodilators (e.g., tiapuride etc.), somatostatin receptor agonists (e.g., BIM23190), apoptosis signal regulating kinase-1 (ASK-1) inhibitors and the like.

Examples of the therapeutic agents for hyperlipidemia include HMG-CoA reductase inhibitors (e.g., pravastatin, simvastatin, lovastatin, atorvastatin, fluvastatin, pitavastatin, rosuvastatin or salts thereof (e.g., sodium salt, calcium salt)), squalene synthase inhibitors (e.g., compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), antioxidants (e.g., lipoic acid, probucol), ACAT inhibitors (e.g., Avasimibe, Eflucimibe), anion exchange resins (e.g., colestyramine), probucol, nicotinic acid drugs (e.g., nicomol, niceritrol), ethyl icosapentate, phytosterols (e.g., soysterol, γ-oryzanol) and the like.

Examples of the antihypertensive agents include angiotensin converting enzyme inhibitors (e.g., captopril, enalapril, delapril), angiotensin II receptor antagonists (e.g., losartan, candesartan cilexetil, eprosartan, valsartan, telmisartan, irbesartan, olmesartan medoxomil, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium channel blockers (e.g., manidipine, nifedipine, amlodipine, efonidipine, nicardipine), potassium channel openers (e.g., levcromakalim, L-27152, AL 0671, NIP-121), clonidine and the like.

Examples of the antiobesity agents include antiobesity agents acting on the central nervous system (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonists (e.g., CP-422935); cannabinoid receptor antagonists (e.g., SR-141716, SR-147778); ghrelin antagonists), 11β-hydroxysteroid dehydrogenase inhibitors (e.g., BVT-3498), pancreatic lipase inhibitors (e.g., orlistat, ATL-962), β3 agonists (e.g., AJ-9677), peptide anorexiants (e.g., leptin, CNTF (Ciliary Neurotropic Factor)), cholecystokinin agonists (e.g., lintitript, FPL-15849), feeding deterrents (e.g., P-57) and the like.

Examples of the diuretics include xanthine derivatives (e.g., sodium salicylate and theobromine, calcium salicylate and theobromine), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzenesulfonamide preparations (e.g., chlortalidone, mefruside, indapamide), azosemide, isosorbide, etacrynic acid, piretanide, bumetanide, furosemide and the like.

Examples of the chemotherapeutic agents include alkylating agents (e.g., cyclophosphamide, ifosfamide), metabolic antagonists (e.g., methotrexate, 5-fluorouracil and a derivative thereof), antitumor antibiotics (e.g., mitomycin, adriamycin), plant-derived antitumor agents (e.g., vincristine, vindesine, Taxol), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivative, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor, erythropoietin) and the like, with preference given to interleukins such as IL-1, IL-2, IL-12 and the like.

Examples of the antiinflammatory agents include non-steroidal antiinflammatory agents such as aspirin, acetaminophen, indomethacin and the like, and the like.

Examples of the antithrombotic agents include heparins (e.g., heparin sodium, heparin calcium, dalteparin sodium), warfarin (e.g., warfarin potassium), anti-thrombin drugs (e.g., aragatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride) and the like.

Examples of the therapeutic agents for osteoporosis include alfacalcidol, calcitriol, elcatonin, calcitonin salmon, estriol, ipriflavone, risedronate disodium, pamidronate disodium, alendronate sodium hydrate, incadronate disodium and the like.

Examples of the vitamins include vitamin $B_1$, vitamin $B_{12}$ and the like.

Examples of the antidementia agents include tacrine, donepezil, rivastigmine, galanthamine and the like.

Examples of the therapeutic agents for pollakiuria or urinary incontinence include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-ameliorating action established in animal models and clinical situations, such as cyclooxygenase inhibitors (e.g., indomethacin), progesterone derivatives (e.g., megestrol acetate), glucosteroids (e.g., dexamethasone), metoclopramide agents, tetrahydrocannabinol agents, fat metabolism improving agents (e.g., eicosapentanoic acid), growth hormones, IGF-1, or antibodies to a cachexia-inducing factor such as TNF-α, LIF, IL-6 and oncostatin M, can be used in combination with the compound of the present invention.

Furthermore, glycosylation inhibitors (e.g., ALT-711), nerve regeneration promoting drugs (e.g., Y-128, VX853, prosaptide), antidepressants (e.g., desipramine, amitriptyline, imipramine), antiepileptics (e.g., lamotrigine, Trileptal, Keppra, Zonegran, Pregabalin, Harkoseride, carbamazepine), antiarrhythmic agents (e.g., mexiletine), acetylcholine receptor agonists (e.g., ABT-594), endothelin receptor antagonists (e.g., ABT-627), monoamine uptake inhibitors (e.g., tramadol), narcotic analgesics (e.g., morphine), GABA receptor agonists (e.g., gabapentin, gabapentin MR agents), α2 receptor agonists (e.g., clonidine), local analgesics (e.g., capsaicin), antianxiety drugs (e.g., benzothiazepine), phosphodiesterase inhibitors (e.g., sildenafil), dopamine receptor agonists (e.g., apomorphine), midazolam, ketoconazole and the like can also be used in combination with the compound of the present invention.

The above-mentioned drug X may be used in a mixture of two or more kinds thereof at an appropriate ratio.

By combining the compound of the present invention with drug X, superior effects such as (1) decreased dose of the compound of the present invention and/or drug X as compared to single administration of the compound of the present invention or drug X,
(2) a synergistic effect afforded by a combined use of the compound of the present invention and drug X, and the like can be achieved.

When the compound of the present invention and drug X are used in combination, the administration time of the compound of the present invention and the drug X is not restricted, and the compound of the present invention and the drug X can be administered to an administration subject simultaneously, or may be administered at staggered times. The dosage of the drug X may be determined according to the dose clinically used, and can be appropriately selected depending on an administration subject, administration route, disease, combination and the like.

The administration mode of the compound of the present invention and the drug X is not particularly restricted, and it is sufficient that the compound of the present invention and the drug X are combined in administration. As such administration mode, the following methods can be mentioned: (1) The compound of the present invention and the drug X are simultaneously formulated to give a single preparation which is administered. (2) The compound of the present invention and the drug X are separately formulated to give two kinds of preparations which are administered simultaneously by the same administration route. (3) The compound of the present invention and the drug X are separately formulated to give two kinds of preparations which are administered by the same administration route at staggered times. (4) The compound of the present invention and the drug X are separately formulated to give two kinds of preparations which are administered simultaneously by the different administration routes. (5) The compound of the present invention and the drug X are separately formulated to give two kinds of preparations which are administered by the different administration routes at staggered times (e.g., the compound of the present invention and the drug X are administered in this order, or in the reverse order), and the like.

EXAMPLES

The present invention is further explained in detail by referring to the following Reference Examples, Examples, Formulation Examples and Experimental Example, which are mere working examples not to be construed as limitative and may be changed without departing from the scope of the present invention.

The term "room temperature" in the following Reference Examples and Examples indicates the range of generally from about 10° C. to about 35° C. As for "%", the yield is in mol/mol %, the solvent used for chromatography is in % by volume and other "%" is in % by weight. OH proton, NH proton etc. that could not be confirmed due to broad peak by proton NMR spectrum are not included in the data.

The other symbols used herein mean the following:
s: singlet
d: doublet
t: triplet
q: quartet
m: multiplet
br: broad
J: coupling constant
Hz : Hertz
$CDCl_3$: deuterated chloroform
$DMSO-d_6$: dimethylsulfoxide-D
$^1H$ NMR: proton nuclear magnetic resonance In the following Reference Examples and Examples, mass spectrum (MS) and nuclear magnetic resonance spectrum (NMR) were measured under the following conditions.
MS measurement tools: ZMD manufactured by Waters Corporation, ZQ2000 manufactured by Waters Corporation or platform II manufactured by Micromass Ltd.
ionization method: Electron Spray Ionization (ESI) or Atmospheric Pressure Chemical Ionization (APCI). Unless specifically indicated, ESI was used.
NMR measurement tools: Varian Gemini 200 (200 MHz) manufactured by Varian, Varian Gemini 300 (300 MHz) manufactured by Varian, AVANCE 300 manufactured by Bruker BioSpin Corp.

In Reference Examples and Examples, purification by preparative HPLC was performed under the following conditions. preparative HPLC tools: high through-put purification system manufactured by Gilson, Inc.
column: YMC Combiprep ODS-A S-5 μm, 20×50 mm solvent:
  Solution A; 0.1% trifluoroacetic acid-containing water,
  Solution B; 0.1% trifluoroacetic acid-containing acetonitrile
gradient cycle A: 0.00 min (Solution A/Solution B=90/10), 1.20 min (Solution A/Solution B=90/10), 4.75 min (Solution A/Solution B=0/100), 7.30 min (Solution A/Solution B=0/100), 7.40 min (Solution A/Solution B=90/10), 7.50 min (Solution A/Solution B=90/10).
gradient cycle B: 0.00 min (Solution A/Solution B=95/5), 1.00 min (Solution A/Solution B=95/5), 5.20 min (Solution A/Solution B=5/95), 6.40 min (Solution A/Solution B=5/95), 6.50 min (Solution A/Solution B=95/5), 6.60 min (Solution A/Solution B=95/5).
flow rate: 25 ml/min,
detection method: UV 220 nm In the present specification, the melting point (m.p.) refers to that measured using, for example, micromelting point measuring apparatus (Büchi, B-545) and the like.

In general, melting points may vary depending on measurement apparatuses, measurement conditions and the like. The crystal in the present specification may show a different melting point from that described in the present specification, as long as it is within the general error range.

Reference Example 1

4'-hydroxy-2',6'-dimethylbiphenyl-3-carbaldehyde

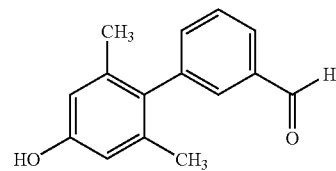

4-Bromo-3,5-dimethylphenol (10.1 g, 50.0 mmol) and (3-formylphenyl)boronic acid (8.25 g, 55.0 mmol) were dissolved in a mixed solution of 1 M aqueous sodium carbonate solution (150 mL), ethanol (50 mL) and toluene (150 mL), and after argon substitution, tetrakis(triphenylphosphine)palladium(0) (2.89 g, 2.50 mmol) was added. The reaction mixture was stirred at 80° C. for 27 hr under argon atmosphere. After cooling the reaction mixture, water and ethyl acetate were added, and the insoluble material was filtered off through celite. The filtrate was separated into an aqueous layer and an organic layer, and the organic layer was washed with saturated brine, dried over anhydrous magnesium sulfate, and concentrated under reduced pressure. The residue was purified by silica gel column chromatography (ethyl acetate:hexane=10:90-40:60), and recrystallized from ethyl acetate-hexane to give the title compound (8.53 g, yield 74%) as colorless prisms.

MS m/z 227 (MH+).

Reference Example 2

4'-(2-ethoxyethoxy)-2',6'-dimethylbiphenyl-3-carbaldehyde

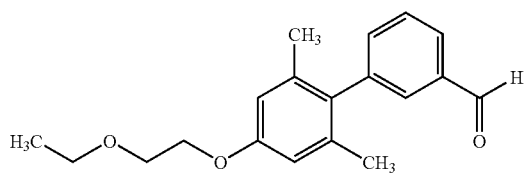

To a solution of 4'-hydroxy-2',6'-dimethylbiphenyl-3-carbaldehyde (8.52 g, 37.7 mmol) and 2-chloroethyl ethyl ether (6.15 g, 56.6 mmol) in N,N-dimethylformamide (40 mL) were added potassium carbonate (6.25 g, 45.2 mmol) and potassium iodide (1.25 g, 7.54 mmol), and the mixture was stirred at 80° C. for 18 hr. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (ethyl acetate:hexane=5:95-25:75) to give the title compound (10.0 g, yield 89%) as a colorless oil.

MS m/z 299 (MH+).

Reference Example 3

[4'-(2-ethoxyethoxy)-2',6'-dimethylbiphenyl-3-yl]methanol

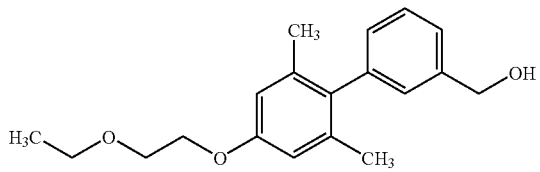

4'-(2-Ethoxyethoxy)-2',6'-dimethylbiphenyl-3-carbaldehyde (2.39 g, 9.70 mmol) was dissolved in a mixed solvent of 1,2-dimethoxyethane (20 mL) and tetrahydrofuran (20 mL). After cooling, sodium borohydride (0.227 g, 6.00 mmol) was added, and the mixture was stirred at the same temperature for 3 hr. Aqueous ammonium chloride solution was added to the reaction mixture, and the mixture was extracted with ethyl acetate. The extract was washed with saturated brine, dried over anhydrous magnesium sulfate, and concentrated under reduced pressure. The residue was purified by silica gel column chromatography (ethyl acetate:hexane=20:80-50:50) to give the title compound (3.55 g, yield 98%) as colorless crystals.

MS m/z 301 (MH+).

Reference Example 4 methyl (2E)-3-(4-{[4'-(2-ethoxyethoxy)-2',6'-dimethylbiphenyl-3-yl]methoxy}phenyl)acrylate

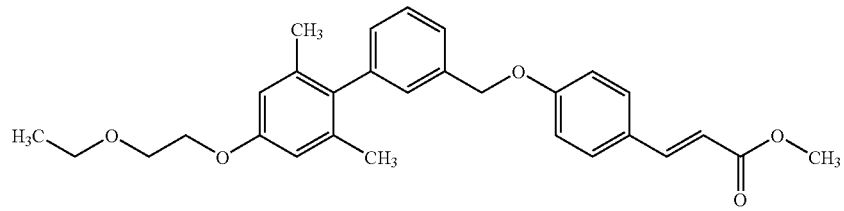

A solution of methyl (2E)-3-(4-hydroxyphenyl)acrylate (0.713 g, 4.00 mmol), [4'-(2-ethoxyethoxy)-2',6'-dimethylbiphenyl-3-yl]methanol (1.20 g, 4.00 mmol) and tributylphosphine (1.29 g, 6.40 mmol) in toluene (65 mL) was stirred, 1,1'-(azodicarbonyl)dipiperidine (1.61 g, 6.40 mmol) was added in small portions, and the mixture was stirred at room temperature for 24 hr. Hexane (35 mL) was added to the reaction mixture. The precipitated insoluble material was filtrated, and the filtrate was concentrated under reduced pressure. The residue was purified by silica gel column chromatography (ethyl acetate:hexane=0:100-25:75), and recrystallized from ethyl acetate-hexane to give the title compound (1.58 g, yield 86%) as colorless crystals.

melting point 69° C.

Reference Example 5 methyl (2E)-3-[4-(acetyloxy)phenyl]acrylate

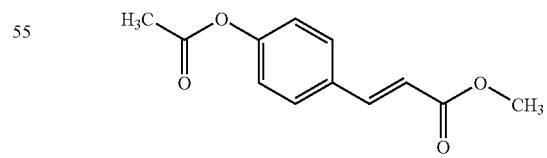

To a solution of methyl (2E)-3-(4-hydroxyphenyl)acrylate (5.35 g, 30.0 mmol) in acetic anhydride (45.0 mL, 476 mmol) was added pyridine (4.85 mL, 60.0 mmol), and the mixture was stirred at room temperature for 26 hr. The reaction mixture was concentrated under reduced pressure. Water was added to the residue, and the mixture was extracted with diethyl ether. The extract was washed with saturated brine, dried over anhydrous magnesium sulfate, and concentrated under reduced pressure. The precipitated crystals were washed with ethyl acetate-hexane to give the title compound (6.15 g, yield 93%) as colorless crystals.

MS m/z 221 (MH+).

Reference Example 6 methyl 2-[4-(acetyloxy)phenyl]cyclopropanecarboxylate

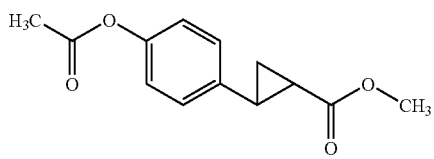

A solution of methyl (2E)-3-[4-(acetyloxy)phenyl]acrylate (2.20 g, 10.0 mmol) in tetrahydrofuran (200 mL) was stirred under ice-cooling, and a solution of diazomethane, prepared from N-methyl-N'-nitro-N-nitrosoguanidine (50% water-containing product, 7.50 g, 51.0 mmol) and aqueous potassium hydroxide (6.28 g, 112 mmol) solution (10.5 mL), in diethyl ether (75 mL) and palladium(II) acetate (0.150 g, 0.668 mmol) were alternately added thereto over 10 min in small portions. The reaction mixture was stirred for 2 hr under ice-cooling, and acetic acid (3 drops) was added. The insoluble material was filtered off through celite, and the filtrate was concentrated under reduced pressure. The residue was purified by silica gel column chromatography (ethyl acetate:hexane=5:95-40:60) to give the title compound (2.26 g, yield 97%) as a colorless oil.

$^1$H NMR (CDCl$_3$) δ: 1.26-1.34(1H, m), 1.57-1.64(1H, m), 1.84-1.92(1H, m), 2.29(3H, s), 2.48-2.57(1H, m), 3.72(3H, s), 6.96-7.03(2H, m), 7.08-7.14(2H, m).

Reference Example 7 methyl 2-(4-hydroxyphenyl)cyclopropanecarboxylate

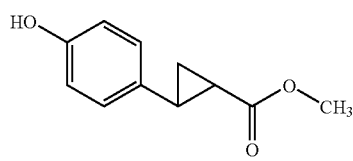

Methyl 2-[4-(acetyloxy)phenyl]cyclopropanecarboxylate (2.26 g, 9.65 mmol) was dissolved in a mixed solvent of methanol (80 mL) and water (20 mL), and ammonium acetate (5.95 g, 77.2 mmol) was added. The mixture was stirred at room temperature for 10 hr and further stirred at 60° C. for 8 hr. The reaction mixture was concentrated under reduced pressure, and the residue was extracted with ethyl acetate. The extract was washed with saturated brine, dried over anhydrous magnesium sulfate, and concentrated under reduced pressure. The residue was purified by silica gel column chromatography (ethyl acetate:hexane=5:95-40:60) to give the title compound (1.78 g, yield 96%) as colorless crystals melting point 69-71° C. .

Reference Example 8

4-(4-bromo-3,5-dimethylphenoxy)tetrahydro-2H-thiopyran

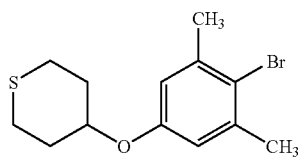

To a solution of 4-bromo-3,5-dimethylphenol (0.201 g, 1.00 mmol), tetrahydro-2H-thiopyran-4-ol (0.130 g, 1.10 mmol) and triphenylphosphine (0.341 g, 1.30 mmol) in tetrahydrofuran (5 mL) was added diethyl azodicarboxylate (40% toluene solution, 0.591 mL, 1.30 mmol), and the mixture was stirred at room temperature for 1.5 hr. Tetrahydro-2H-thiopyran-4-ol (0.0591 g, 0.500 mmol), triphenylphosphine (0.157 g, 0.600 mmol) and diethyl azodicarboxylate (40% toluene solution, 0.272 mL, 0.600 mmol) were added, and the mixture was further stirred for 1.5 hr. The reaction mixture was concentrated under reduced pressure, and the residue was purified by silica gel column chromatography (ethyl acetate:hexane=0:100-20:80) to give the title compound (0.261 g, yield 86%) as colorless crystals.

$^1$H NMR (CDCl$_3$) δ: 1.93-2.07(2H, m), 2.10-2.23(2H, m), 2.37(6H, s), 2.49-2.61(2H, m), 2.85-2.98(2H, m), 4.26-4.35 (1H, m), 6.65(2H, s).

Reference Example 9

[2,6-dimethyl-4-(tetrahydro-2H-thiopyran-4-yloxy) phenyl]boronic acid

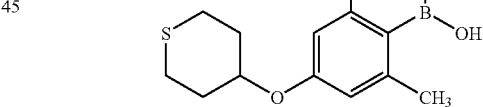

To a solution of 4-(4-bromo-3,5-dimethylphenoxy)tetrahydro-2H-thiopyran (3.01 g, 10.0 mmol) in tetrahydrofuran (50 mL) was added dropwise a hexane solution (1.6 M, 6.57 mL, 10.5 mmol) of n-butyllithium at −78° C. The reaction mixture was stirred at the same temperature for 1.5 hr, and triisopropyl borate (6.92 mL, 30.0 mmol) was added. After warming to room temperature, the mixture was stirred overnight. The reaction mixture was ice-cooled, 2 M hydrochloric acid (50 mL) was added, and the mixture was stirred for 2.5 hr. The mixture was separated into the aqueous layer and the organic layer. The organic layer was washed with saturated brine and saturated aqueous sodium hydrogencarbonate while adjusting to neutral, dried over anhydrous magnesium sulfate, and concentrated under reduced pressure. The residue was washed with cold hexane to give the title compound (1.89 g, yield 71%) as colorless crystals.

$^1$NMR (CDCl$_3$) δ: 1.90-2.06(2H, m), 2.09-2.23(2H, m), 2.35(6H, s), 2.48-2.62(2H, m), 2.83-2.98(2H, m), 4.28-4.40 (1H, m), 6.51(2H, s), 6.59(2H, s).

Reference Example 10 methyl 2',6'-dimethyl-4'-(tetrahydro-2H-thiopyran-4-yloxy)biphenyl-3-carboxylate

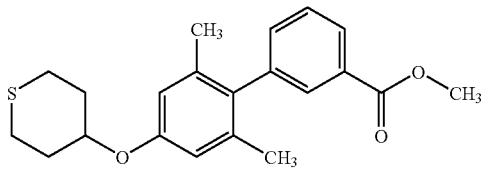

In the same manner as in Reference Example 1, the title m compound was obtained as colorless crystals from [2,6-dimethyl-4-(tetrahydro-2H-thiopyran-4-yloxy)phenyl]boronic acid and methyl 3-bromobenzoate. yield 86%.

melting point 69-71° C.

Reference Example 11 methyl 4'-[(1,1-dioxidotetrahydro-2H-thiopyran-4-yl)oxy]-2',6'-dimethylbiphenyl-3-carboxylate

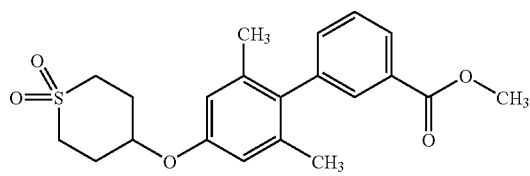

To a solution of methyl 2',6'-dimethyl-4'-(tetrahydro-2H-thiopyran-4-yloxy)biphenyl-3-carboxylate (1.56 g, 4.38 mmol) in ethyl acetate (20 mL) was added m-chloroperbenzoic acid (65%, 2.44 g, 9.20 mmol) under ice-cooling, and the mixture was stirred for 16 hr while allowing the mixture to gradually warm to room temperature. Ethyl acetate was added to the reaction mixture. The mixture was washed with a mixed solution of saturated aqueous sodium hydrogencarbonate and aqueous thiosodium sulfate solution, further washed with saturated brine, dried over anhydrous magnesium sulfate, and concentrated under reduced pressure. The residue was recrystallized from ethyl acetate-hexane to give the title compound (1.45 g, yield 85%) as colorless crystals.

melting point 180° C.

Reference Example 12

{4'-[(1,1-dioxidotetrahydro-2H-thiopyran-4-yl)oxy]-2',6'-dimethylbiphenyl-3-yl}methanol

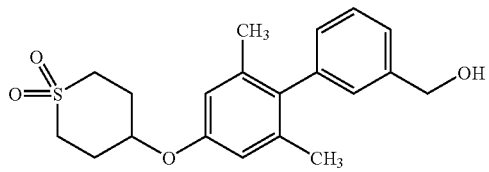

To a solution of methyl 4'-[(1,1-dioxidotetrahydro-2H-thiopyran-4-yl)oxy]-2',6'-dimethylbiphenyl-3-carboxylate (0.128 g, 0.33 mmol) in tetrahydrofuran (2 mL) was added lithium aluminum hydride (80%, 15.7 mg, 0.33 mmol) in small portions under ice-cooling, and the mixture was stirred at the same temperature for 1.5 hr. Sodium sulfate 10 hydrate (0.106 g, 0.33 mmol) was added to the reaction mixture in small portions, and the mixture was stirred at room temperature for 1 hr. The insoluble material was filtered off through celite, and the filtrate was concentrated under reduced pressure to give the title compound (0.111 g, yield 93%) as a colorless amorphous powder.

$^1$H NMR (CDCl$_3$) δ: 1.76(1H, t, J=5.6 Hz), 2.00(6H, s), 2.29-2.44(2H, m), 2.44-2.58(2H, m), 2.87-3.02(2H, m), 3.37-3.53(2H, m), 4.63-4.70(1H, m), 4.74(2H, d, J=5.6 Hz), 6.68 (2H, s), 7.05(1H, dt, J=7.4, 1.5 Hz), 7.12(1H, s), 7.31-7.38 (1H, m), 7.42(1H, t, J=7.4 Hz).

Reference Example 13

2',6'-dimethyl-4'-[(3-methyloxetan-3-yl)methoxy]biphenyl-3-carbaldehyde

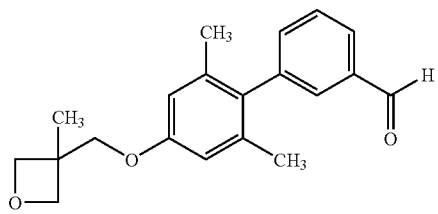

In the same manner as in Reference Example 2, the title compound was obtained as a colorless oil from 4'-hydroxy-2',6'-dimethylbiphenyl-3-carbaldehyde. yield 98%.

$^1$H NMR (CDCl$_3$) δ: 1.46(3H, s), 2.01(6H, s), 4.06(2H, s), 4.48(2H, d, J=5.8 Hz), 4.65(2H, d, J=5.8 Hz), 6.73(2H, s), 7.42(1H, dt, J=7.6, 1.4 Hz), 7.59(1H, t, J=7.6 Hz), 7.67(1H, t, J=1.4 Hz), 7.87(1H, dt, J=7.6, 1.4 Hz), 10.05(1H, s).

Reference Example 14

{2',6'-dimethyl-4'-[(3-methyloxetan-3-yl)methoxy]biphenyl-3-yl)methanol

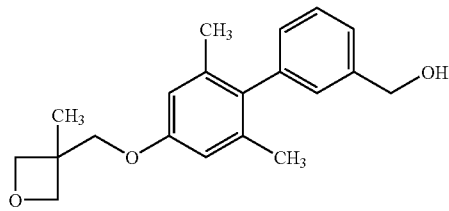

In the same manner as in Reference Example 3, the title compound was obtained as colorless crystals from 2',6'-dimethyl-4'-[(3-methyloxetan-3-yl)methoxy]biphenyl-3-carbaldehyde. yield 92%.

MS m/z 313 (MH$^+$).

Reference Example 15

N-(3-methylbutyl)-4-[4-(trifluoromethyl)phenyl]-1,3-thiazole-2-amine

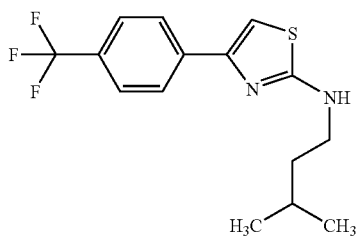

A solution of N-(3-methylbutyl)thiourea (3.00 g, 20.5 mmol), 2-bromo-1-[4-(trifluoromethyl)phenyl]ethanone (5.45 g, 20.5 mmol) and sodium acetate (2.19 g, 26.7 mmol) in ethanol (50 mL) was stirred at 90° C. for 4 hr. The reaction mixture was poured into water, and the mixture was extracted with ethyl acetate. The extract was dried over anhydrous sodium sulfate and concentrated under reduced pressure. The obtained solid was recrystallized from dichloromethane-hexane to give the title compound (1.76 g, yield 27%) as pale-yellow crystals.

$^1$H NMR (CDCl$_3$) δ: 0.95(6H, d, J=6.5 Hz), 1.55(2H, q, J=7.0 Hz), 1.63-1.79(1H, m), 3.24-3.36(2H, m), 5.29(1H, br s), 6.80(1H, s), 7.61(2H, d, J=8.3 Hz), 7.90(2H, d, J=8.3 Hz).

Reference Example 16 methyl 4-[((3-methylbutyl){4-[4-(trifluoromethyl)phenyl]-1,3-thiazol-2-yl}amino)methyl]benzoate

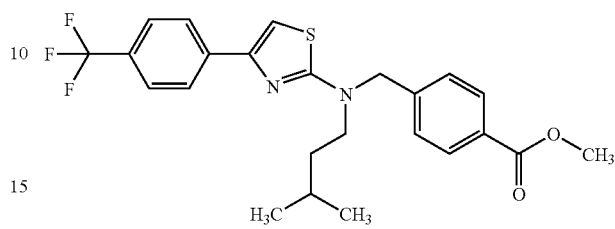

To a solution of N-(3-methylbutyl)-4-[4-(trifluoromethyl)phenyl]-1,3-thiazole-2-amine (1.20 g, 3.82 mmol) in N,N-dimethylformamide (20 mL) was added sodium hydride (60% in oil, 0.229 g, 5.73 mmol). The mixture was stirred for 30 min, and methyl 4-(bromomethyl)benzoate (1.05 g, 4.58 mmol) was added. The mixture was stirred at 60° C. for 1.5 hr, water was added to the reaction mixture, and the mixture was extracted with ethyl acetate. The extract was washed with saturated brine and concentrated under reduced pressure. The residue was purified by silica gel column chromatography (ethyl acetate:hexane=3:97-40:60) to give the title compound (1.34 g, yield 76%) as a yellow oil.

MS m/z 463 (MH$^+$).

Reference Example 17

{4-[((3-methylbutyl){4-[4-(trifluoromethyl)phenyl]-1,3-thiazol-2-yl}amino)methyl]phenyl}methanol

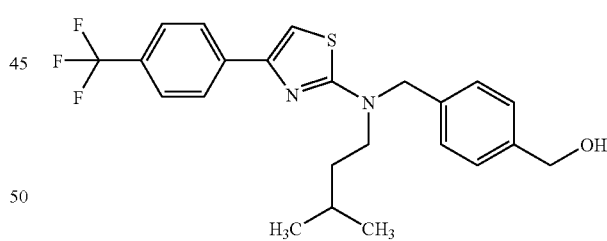

To a solution of methyl 4-[((3-methylbutyl){4-[4-(trifluoromethyl)phenyl]-1,3-thiazol-2-yl}amino)methyl]benzoate (1.34 g, 2.90 mmol) in tetrahydrofuran (10 mL) was added dropwise a toluene solution (1.0 M, 6.38 mL, 6.38 mmol) of diisobutylaluminum hydride under ice-cooling. The reaction mixture was stirred at room temperature for 2 hr, sodium sulfate 10 hydrate was added, and the mixture was further stirred for 1 hr. The insoluble material was filtered, and the filtrate was concentrated under reduced pressure. The residue was purified by silica gel column chromatography (ethyl acetate:hexane=10:90-60:40) to give the title compound (0.950 g, yield 75%) as a colorless oil.

MS m/z 435 (MH$^+$).

Reference Example 18

N-propyl-4-[4-(trifluoromethyl)phenyl]-1,3-thiazole-2-amine

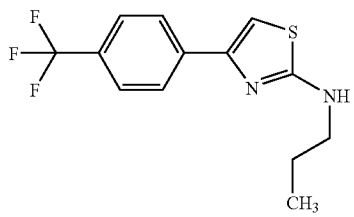

In the same manner as in Reference Example 15, the title compound was obtained as pale-yellow crystals from 2-bromo-1-[4-(trifluoromethyl)phenyl]ethanone and N-propylthiourea. yield 77%.
MS m/z 287 (MH$^+$).

Reference Example 19 methyl 4-[(propyl{4-[4-(trifluoromethyl)phenyl]-1,3-thiazol-2-yl}amino)methyl]benzoate

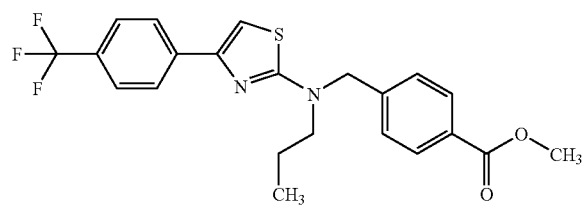

In the same manner as in Reference Example 16, the title compound was obtained as colorless crystals from methyl N-propyl-4-[4-(trifluoromethyl)phenyl]-1,3-thiazole-2-amine and 4-(bromomethyl)benzoate. yield 41%.
MS m/z 435 (MH$^+$).

Reference Example 20

{4-[(propyl{4-[4-(trifluoromethyl)phenyl]-1,3-thiazol-2-yl}amino)methyl]phenyl}methanol

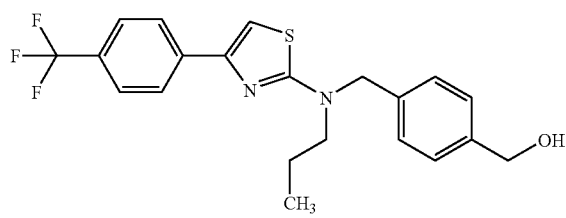

In the same manner as in Reference Example 17, the title compound was obtained as colorless crystals from methyl 4-[propyl}4-[4-(trifluoromethyl)phenyl]-1,3-thiazol-2-yl}amino)methyl]benzoate. yield 85%.
MS m/z 407 (MH$^+$).

Reference Example 21 ethyl (2E)-3-(4-amino-2-fluorophenyl)acrylate

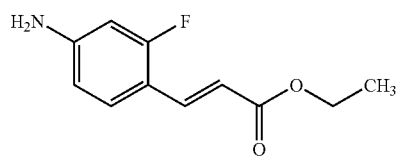

To a mixture of 4-bromo-3-fluoroaniline (13.3 g, 70.0 mmol), ethyl acrylate (9.48 mL, 87.5 mmol), tris(2-methylphenyl)phosphine (8.52 g, 28.0 mmol), N,N-diisopropylethylamine (50 mL) and N,N-dimethylformamide (50 mL) was added palladium(II) acetate (0.786 g, 3.50 mmol), and the mixture was stirred at 110° C. for 5 hr under an argon atmosphere. The reaction mixture was cooled, and the solvent was evaporated under reduced pressure. Water and ethyl acetate were added to the residue, and the insoluble material was filtered off through celite. The filtrate was separated into the aqueous layer and the organic layer. The organic layer was washed with saturated brine, dried over anhydrous magnesium sulfate, and concentrated under reduced pressure. The residue was purified by silica gel column chromatography (ethyl acetate:hexane=20:80-60:40) to give the title compound (14.0 g, yield 96%). A part thereof was recrystallized to give yellow prisms.
MS m/z 210 (MH$^+$).

Reference Example 22 ethyl 2-(4-amino-2-fluorophenyl)cyclopropanecarboxylate

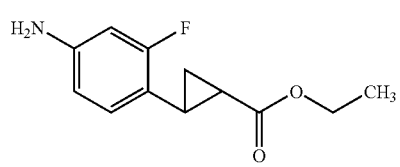

In the same manner as in Reference Example 6, the title compound was obtained as a brown oil from ethyl (2E)-3-(4-amino-2-fluorophenyl)acrylate. yield 65%.
MS m/z 224 (MH$^+$).

Example 1 methyl 2-(4-{(4'-(2-ethoxyethoxy)-2',6'-dimethylbiphenyl-3-yl]methoxy}phenyl)cyclopropanecarboxylate

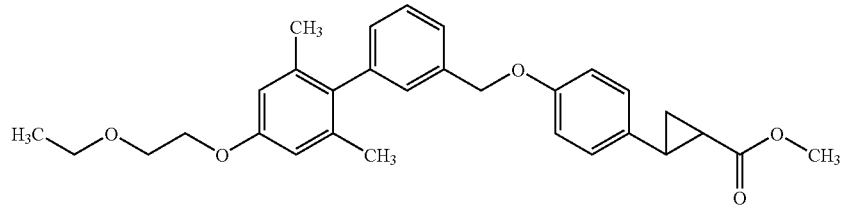

A solution of methyl (2E)-3-(4-{[4'-(2-ethoxyethoxy)-2',6'-dimethylbiphenyl-3-yl]methoxy}phenyl)acrylate (1.50 g, 3.26 mmol) in tetrahydrofuran (50 mL) was stirred under ice-cooling, and a solution of diazomethane prepared from N-methyl-N'-nitro-N-nitrosoguanidine (50% water-containing product, 4.98 g, 16.9 mmol) and 9.5 M aqueous potassium hydroxide solution (12.0 mL, 114 mmol) in diethyl ether (25 mL), and palladium(II) acetate (36.6 mg, 0.163 mmol) were alternately added thereto over 10 min in small portions. The reaction mixture was stirred for 5 hr, and acetic acid (3 drops) was added. The insoluble material was filtered off through celite, and the filtrate was concentrated under reduced pressure. The residue was purified by silica gel column chromatography (ethyl acetate:hexane=0:100-30:70) to give the title compound (1.53 g, yield 99%) as a colorless oil.

$^1$H NMR (CDCl$_3$) δ: 1.22-1.30(4H, m), 1.52-1.60(1H, m), 1.78-1.86(1H, m), 1.98(6H, s), 2.44-2.53(1H, m), 3.62(2H, q, J=7.0 Hz), 3.71(3H, s), 3.80(2H, t, J=5.0 Hz), 4.14(2H, t, J=5.0 Hz), 5.07(2H, s), 6.69(2H, s), 6.85-6.92(2H, m), 6.99-7.05(2H, m), 7.08(1H, d, J=7.0 Hz), 7.17(1H, s), 7.35-7.45(2H, m).

Example 2

2-(4-{[4'-(2-ethoxyethoxy)-2',6'-dimethylbiphenyl-3-yl]methoxy}phenyl)cyclopropanecarboxylic acid

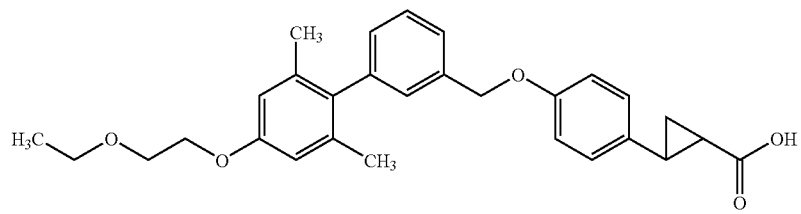

To a mixed solution of methyl 2-(4-{[4'-(2-ethoxyethoxy)-2',6'-dimethylbiphenyl-3-yl]methoxy}phenyl)cyclopropanecarboxylate (1.33 g, 2.80 mmol) in methanol (6 mL) and tetrahydrofuran (12 mL) was added 2 M aqueous sodium hydroxide solution (3 and the mixture was stirred at 50° C. for 2 hr. Water was added to the reaction mixture, and the mixture was acidified with 1 M hydrochloric acid and extracted with ethyl acetate. The extract was washed with saturated brine, dried over anhydrous magnesium sulfate, and concentrated under reduced pressure. The residue was purified by silica gel column chromatography (ethyl acetate:hexane=20:80-70:30) to give the title compound (1.29 g, quantitative) as a colorless oil.

¹H NMR (CDCl₃) δ: 1.25(3H, t, J=7.0 Hz), 1.31-1.39(1H, m), 1.57-1.65(1H, m), 1.78-1.86(1H, m), 1.98(6H, s), 2.51-2.60(1H, m), 3.62(2H, q, J=7.0 Hz), 3.80(2H, t, J=5.0 Hz), 4.14(2H, t, J=5.0 Hz), 5.08(2H, s), 6.69(2H, s), 6.86-6.92(2H, m), 7.00-7.06(2H, m), 7.06-7.11(1H, m), 7.17(1H, s), 7.35-7.45(2H, m).

Example 3

2-(4-{[4'-(2-ethoxyethoxy)-2',6'-dimethylbiphenyl-3-yl]methoxy}phenyl)cyclopropanecarboxylic acid calcium salt

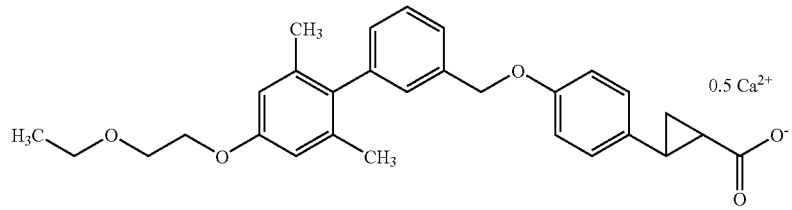

To a solution of 2-(4-{[4'-(2-ethoxyethoxy)-2',6'-dimethylbiphenyl-3-yl]methoxy}phenyl)cyclopropanecarboxylic acid (1.27 g, 2.76 mmol) in methanol (8 mL) was added 1 M aqueous sodium hydroxide solution (2.76 mL, 2.76 mmol). An aqueous solution (2 mL) of calcium chloride (0.153 g, 1.38 mmol) was added thereto. The precipitated solid was collected by filtration, washed with water, and dried to give the title compound (1.28 g, yield 97%) as colorless crystals.

¹H NMR (DMSO-d₆) δ: 0.82-0.92(1H, m), 1.13(3H, t, J=7.0 Hz), 1.19-1.30(1H, m), 1.43-1.54(1H, m), 1.89(6H, s), 2.09-2.19(1H, m), 3.50(2H, q, J=7.0 Hz), 3.65-3.71(2H, m), 4.03-4.10(2H, m), 5.08(2H, s), 6.69(2H, s), 6.81-6.89(2H, m), 6.90-6.97(2H, m), 7.03(1H, d, J=7.2 Hz), 7.12(1H, s), 7.33-7.46(2H, m).

Example 4 methyl 2-[4-({4'-[(1,1-dioxidotetrahydro-2H-thiopyran-4-yl)oxy]-2',6'-dimethylbiphenyl-3-yl}methoxy)phenyl]cyclopropanecarboxylate A solution of methyl 2-(4-hydroxyphenyl)cyclopropanecarboxylate (0.156 g, 0.813 mmol), {4'-[(1,1-dioxidotetrahydro-2H-thiopyran-4-yl)oxy]-2',6'-dimethylbiphenyl-3-yl}methanol (0.395 g, 0.739 mmol) and tributylphosphine (0.298 g, 1.47 mmol) in toluene (15 mL) was stirred, 1,1'-(azodicarbonyl)dipiperidine (0.372 g, 1.47 mmol) was added, and the mixture was stirred at room temperature for 4 hr. Hexane (15 mL) was added to the reaction mixture and the precipitated insoluble material was filtrated. The filtrate was concentrated under reduced pressure and the residue was purified by silica gel column chromatography (ethyl acetate:hexane=20:80-40:60) to give the title compound (0.396 g, yield 91%) as a colorless oil.

MS m/z 535 (MH⁺).

Example 5

2-[4-({4'-[(1,1-dioxidotetrahydro-2H-thiopyran-4-yl)oxy]-2',6'-dimethylbiphenyl-3-yl}methoxy)phenyl]cyclopropanecarboxylic acid

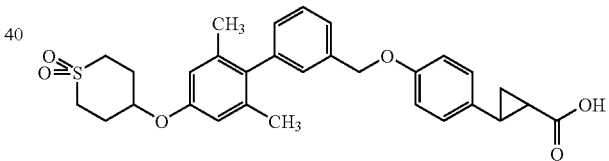

To a mixed solution of methyl 2-[4-({4'-[(1,1-dioxidotetrahydro-2H-thiopyran-4-yl)oxy]-2',6'-dimethylbiphenyl-3-yl}methoxy)phenyl]cyclopropanecarboxylate (0.392 g, 0.733 mmol) in methanol (6 mL) and tetrahydrofuran (12 mL) was added 2 M aqueous sodium hydroxide solution (3

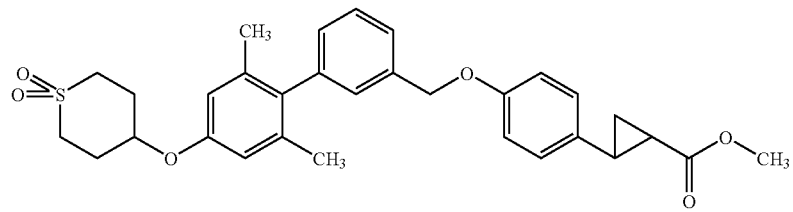

mL), and the mixture was stirred at 50° C. for 2 hr. 1 M Hydrochloric acid (10 mL) was added to the reaction mixture, and the mixture was extracted with ethyl acetate. The extract was washed with saturated brine, dried over anhydrous magnesium sulfate, and concentrated under reduced pressure. The residue was purified by silica gel column chromatography (ethyl acetate:hexane=50:50-90:10) and recrystallized from ethyl acetate-hexane to give the title compound (0.129 g, yield 34%) as colorless crystals. melting point 161-162° C.

Example 6 methyl 2-[4-({2',6'-dimethyl-4'-[(3-methyloxetan-3-yl)methoxy]biphenyl-3-yl}methoxy)phenyl]cyclopropanecarboxylate

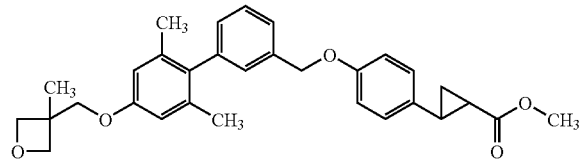

A solution of methyl 2-(4-hydroxyphenyl)cyclopropanecarboxylate (0.157 g, 0.816 mmol), (2',6'-dimethyl-4'-[(3-methyloxetan-3-yl)methoxy]biphenyl-3-yl}methanol (0.231 g, 0.741 mmol) and tributylphosphine (0.298 g, 1.47 mmol) in toluene (15 mL) was stirred, 1,1'-(azodicarbonyl)dipiperidine (0.372 g, 1.47 mmol) was added, and the mixture was stirred at room temperature for 4 hr. Hexane (15 mL) was added to the reaction mixture, and the precipitated insoluble material was filtrated. The filtrate was concentrated under reduced pressure and the residue was purified by silica gel column chromatography (ethyl acetate:hexane=10:90-40:60) to give the title compound (0.326 g, yield 82%) as a colorless oil.

$^1$H NMR (CDCl$_3$) δ: 1.20-1.34(1H, m), 1.45(3H, s), 1.50-1.62(1H, m), 1.75-1.88(1H, m), 1.99(6H, s), 2.40-2.57(1H, m), 3.66-3.78(3H, m), 4.04(2H, s), 4.47(2H, d, J=5.8 Hz), 4.64(2H, d, J=5.8 Hz), 5.08(2H, s), 6.70(2H, s), 6.89(2H, d, J=8.7 Hz), 7.02(2H, d, J=8.7 Hz), 7.08(1H, d, J=6.9 Hz), 7.17(1H, s), 7.32-7.49(2H, m).

Example 7

2-[4-({2',6'-dimethyl-4'-[(3-methyloxetan-3-yl)methoxy]biphenyl-3-yl}methoxy)phenyl]cyclopropanecarboxylic acid

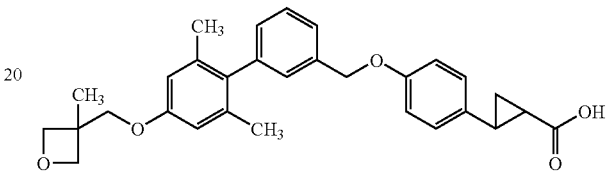

In the same manner as in Example 5, the title compound was obtained as a colorless oil from methyl 2-[4-({2',6'-dimethyl-4'-[(3-methyloxetan-3-yl)methoxy]biphenyl-3-yl}methoxy)phenyl]cyclopropanecarboxylate. yield 82%.

$^1$H NMR (CDCl$_3$) δ: 1.30-1.39(1H, m), 1.45(3H, s), 1.54-1.67(1H, m), 1.76-1.87(1H, m), 1.95-2.02(6H, m), 2.46-2.64(1H, m), 4.04(2H, s), 4.47(2H, d, J=5.8 Hz), 4.65(2H, d, J=5.8 Hz), 5.09(2H, s), 6.66-6.74(2H, m), 6.83-6.95(2H, m), 6.95-7.12(3H, m), 7.17(1H, s), 7.33-7.50(2H, m).

Example 8 methyl 2-[4-({4-[((3-methylbutyl){4-[4-(trifluoromethyl)phenyl]-1,3-thiazol-2-yl}amino)methyl]benzyl}oxy)phenyl]cyclopropanecarboxylate

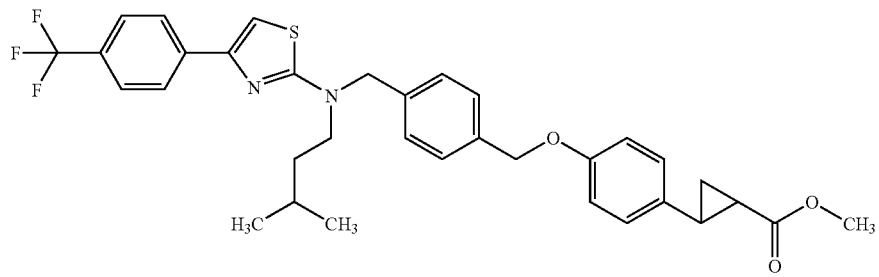

A solution of methyl 2-(4-hydroxyphenyl)cyclopropanecarboxylate (0.152 g, 0.790 mmol), {4-[((3-methylbutyl){4-[4-(trifluoromethyl)phenyl]-1,3- thiazol-2-yl}amino)methyl]phenyl}methanol (0.312 g, 0.718 mmol) and tributylphosphine (0.291 g, 1.44 mmol) in toluene (15 mL) was stirred, 1,1'-(azodicarbonyl)dipiperidine (0.363 g, 1.44 mmol) was added, and the mixture was stirred at room temperature for 60 hr. Hexane (15 mL) was added to the reaction mixture, and the precipitated insoluble material was filtrated. The filtrate was concentrated under reduced pressure and the residue was purified by silica gel column chromatography (ethyl acetate:hexane=0:100-30:70) to give the title compound (0.202 g, yield 42%) as a colorless oil.

$^1$H NMR (CDCl$_3$) δ: 0.95(6H, d, J=5.6 Hz), 1.20-1.31(1H, m), 1.51-1.64(4H, m), 1.76-1.87(1H, m), 2.42-2.53(1H, m), 3.40-3.52(2H, m), 3.71(3H, s), 4.76(2H, s), 5.02(2H, s), 6.78-6.83(1H, m), 6.88(2H, d, J=8.9 Hz), 7.02(2H, d, J=8.9 Hz), 7.30-7.46(4H, m), 7.61(2H, d, J=8.1 Hz), 7.94(2H, d, J=8.1 Hz).

Example 9

2-[4-({4-[((3-methylbutyl){4-[4-(trifluoromethyl)phenyl-1,3-thiazol-2-yl}amino)methyl]benzyl}oxy)phenyl]cyclopropanecarboxylic acid

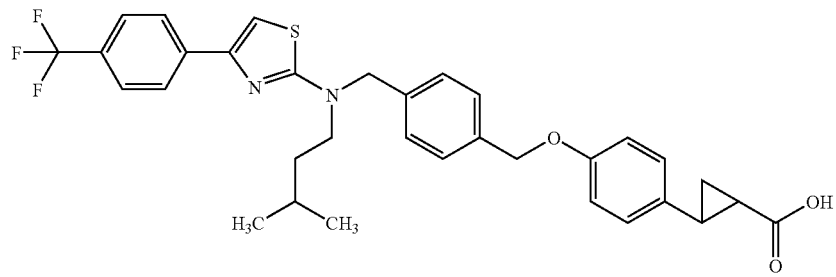

In the same manner as in Example 5, the title compound was obtained as colorless crystals from methyl 2-[4-({4-[((3-methylbutyl){4-[4-(trifluoromethyl)phenyl]-1,3-thiazol-2-yl}amino)methyl]benzyl}oxy)phenyl]cyclopropanecarboxylate. yield 75%.

MS m/z 595 (MH$^+$).

Example 10 methyl 2-[4-({4-[(propyl{4-[4-(trifluoromethyl)phenyl]-1,3-thiazol-2-yl}amino)methyl]benzyl}oxy)phenyl]cyclopropanecarboxylate

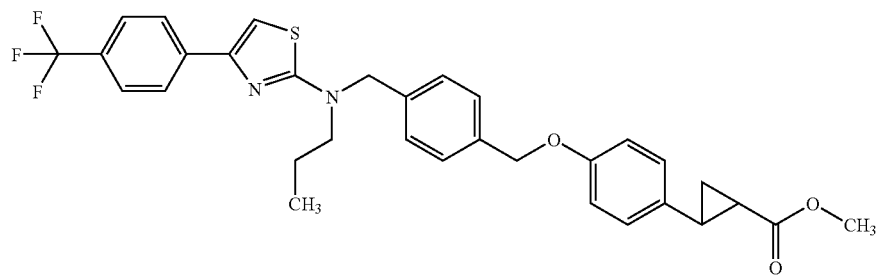

A solution of methyl 2-(4-hydroxyphenyl)cyclopropanecarboxylate (0.158 g, 0.822 mmol), {4-[(propyl{4-[4-(trifluoromethyl)phenyl]-1,3-thiazol-2-yl}amino)methyl]phenyl}methanol (0.303 g, 0.745 mmol) and tributylphosphine (0.301 g, 1.49 mmol) in toluene (15 mL) was stirred, 1,1'-(azodicarbonyl)dipiperidine (0.375 g, 1.49 mmol) was added, and the mixture was stirred at room temperature for 4 hr. Hexane (15 ml) was added to the reaction mixture, and the precipitated insoluble material was filtrated. The filtrate was concentrated under reduced pressure and the residue was purified by silica gel column chromatography (ethyl acetate:hexane=0:100-30:70) to give the title compound (0.366 g, yield 77%) as a colorless oil.

$^1$H NMR (CDCl$_3$) δ: 0.94(3H, t, J=7.4 Hz), 1.16-1.35(1H, m), 1.48-1.62(1H, m), 1.62-1.77(2H, m), 1.77-1.89(1H, m), 2.41-2.59(1H, m), 3.41(2H, t, J=7.8 Hz), 3.71(3H, s), 4.79 (2H, s), 5.02(2H, s), 6.81(1H, s), 6.88(2H, d, J=8.7 Hz), 7.02(2H, d, J=8.7 Hz), 7.31-7.48(4H, m), 7.60(2H, d, J=8.1 Hz), 7.94(2H, d, J=8.1 Hz).

Example 11

2-[4-({4-[(propyl{4-[4-(trifluoromethyl)phenyl]-1,3-thiazol-2-yl}amino)methyl]benzyl}oxy)phenyl]cyclopropanecarboxylic acid

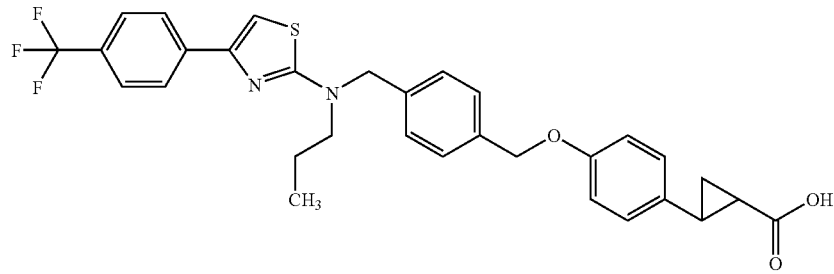

In the same manner as in Example 5, the title compound was obtained as colorless crystals from methyl 2-[4-({4-[(propyl{4-[4-(trifluoromethyl)phenyl]-1,3-thiazol-2-yl}amino)methyl]benzyl}oxy)phenyl]cyclopropanecarboxylate. yield 76%.

MS m/z 567 (MH$^+$).

Example 12 methyl 2-{4-[(3-phenoxybenzyl)oxy]phenyl}cyclopropanecarboxylate

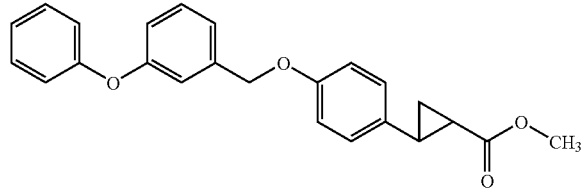

A solution of methyl 2-(4-hydroxyphenyl)cyclopropanecarboxylate (0.158 g, 0.822 mmol), (3-phenoxyphenyl)methanol (0.150 g, 0.747 mmol) and tributylphosphine (0.301 g, 1.49 mmol) in toluene (15 mL) was stirred, 1,1'-(azodicarbonyl)dipiperidine (0.375 g, 1.49 mmol) was added, and the mixture was stirred at room temperature for 60 hr. Hexane (15 mL) was added to the reaction mixture, and the precipitated insoluble material was filtrated. The filtrate was concentrated under reduced pressure and the residue was purified by silica gel column chromatography (ethyl acetate:hexane=0:100-30:70) to give the title compound (0.221 g, yield 72%) as colorless crystals.

melting point 55-56° C.

Example 13

2-{4-[(3-phenoxybenzyl)oxy]phenyl)cyclopropanecarboxylic acid

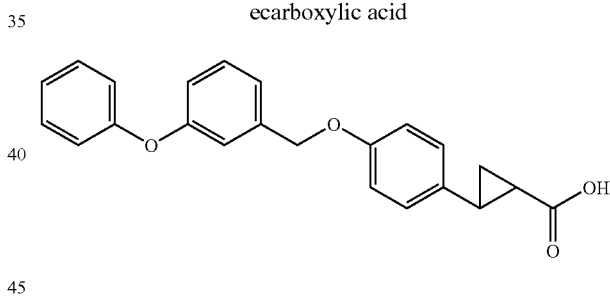

In the same manner as in Example 5, the title compound was obtained as colorless crystals from methyl 2-{4-[(3-phenoxybenzyl)oxy]phenyl}cyclopropanecarboxylate. yield 75%.

melting point 105-106° C.

Example 14 ethyl 2-[4-({[4'-(2-ethoxyethoxy)-2',6'-dimethylbiphenyl-3-yl]methyl}amino)-2-fluorophenyl]cyclopropanecarboxylate

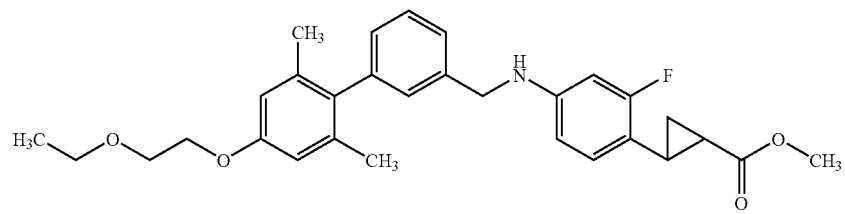

A mixture of 4'-(2-ethoxyethoxy)-2',6'-dimethyl-3-biphenylcarbaldehyde (0.313 g, 1.05 mmol), ethyl 2-(4-amino-2-fluorophenyl)cyclopropanecarboxylate (0.234 g, 1.05 mmol), acetic acid (0.126 g, 2.10 mmol) and 1,2-dichloroethane (5 mL) was stirred under a nitrogen atmosphere at room temperature for 3 hr. Sodium triacetoxyborohydride (0.445 g, 2.10 mmol) was added to the reaction mixture by small portions, and the mixture was stirred for 3.5 hr. The reaction mixture was concentrated under reduced pressure. Water was added to the residue, and the mixture was extracted with ethyl acetate. The extract was washed with saturated brine, dried over anhydrous sodium sulfate, and concentrated under reduced pressure. The residue was purified by silica gel column chromatography (ethyl acetate:hexane=5:95-30:70) to give the title compound (0.456 g, yield 86%) as a yellow oil.
MS m/z 506 (MH$^+$).

Example 15

2-[4-({[4'-(2-ethoxyethoxy)-2',6'-dimethylbiphenyl-3-yl]methyl}amino)-2-fluorophenyl]cyclopropanecarboxylic acid hydrochloride

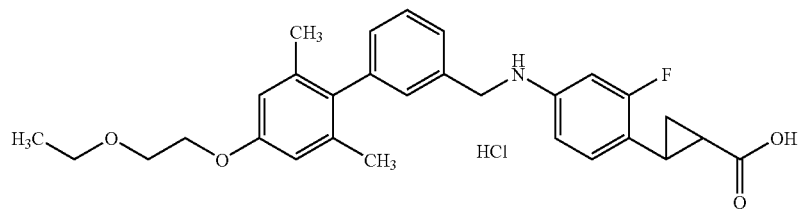

To a mixed solution of ethyl 2-[4-({[4'-(2-ethoxyethoxy)-2',6'-dimethylbiphenyl-3-yl]methyl}amino)-2-fluorophenyl]cyclopropanecarboxylate (0.451 g, 0.892 mmol) in ethanol (2 mL) and tetrahydrofuran (4 mL) was added 2 M aqueous sodium hydroxide solution (1 mL), and the mixture was stirred at 50° C. for 7 hr. Water was added to the reaction mixture, and the mixture was mildly-acidified with 10% aqueous citric acid solution and extracted with ethyl acetate. The extract was washed with saturated brine, dried over anhydrous sodium sulfate, and concentrated under reduced pressure. The residue was purified by silica gel column chromatography (ethyl acetate:hexane=30:70-100:0) to give a yellow oil. To a solution of the obtained oil in ethyl acetate (3.2 mL) was added 4 M hydrogen chloride/ethyl acetate solution (0.8 mL) and the mixture was concentrated under reduced pressure. The residue was crystallized from diethyl ether-ethyl acetate to give the title compound (0.349 g, yield 73%) as colorless crystals.
$^1$H NMR (CDCl$_3$) δ: 1.21-1.33(4H, m), 1.57-1.65(1H, m), 1.75-1.84(7H, m), 2.51-2.60(1H, m), 3.61(2H, q, J=7.0 Hz), 3.76-3.82(2H, m), 4.07-4.13(2H, m), 4.45(2H, s), 6.62(2H, s), 6.73-6.82(2H, m), 6.89(1H, d, J=9.8 Hz), 7.00(1H, d, J=8.5 Hz), 7.09(1H, d, J=7.7 Hz), 7.41(1H, t, J=7.7 Hz), 7.56(1H, d, J=7.7 Hz).

Formulation Example 1

Production of Capsule

| 1) compound of Example 1 | 30 mg |
| 2) microcrystalline cellulose | 10 mg |
| 3) lactose | 19 mg |
| 4) magnesium stearate | 1 mg |
| total | 60 mg |

The above-mentioned 1), 2), 3) and 4) are mixed and filled in a gelatin capsule.

Formulation Example 2

Production of Tablet

| 1) compound of Example 1 | 30 g |
| 2) lactose | 50 g |
| 3) corn starch | 15 g |
| 4) carboxymethylcellulose calcium | 44 g |
| 5) magnesium stearate | 1 g |
| 1000 tablets total | 140 g |

The total amount of the above-mentioned 1), 2) and 3) and 30 g of 4) are kneaded with water, vacuum dried and granulated. The granulated powder is mixed with 14 g of 4) and 1 g of 5) and tableted with a tableting machine. In this way, 1000 tablets containing 30 mg of the compound of Example 1 per tablet are obtained.

Experimental Example 1

Receptor Function Modulating Action (Agonist Action) against Human-Derived GPR40

For determination of agonist activity, CHO cell line that stably expressed human GPR40 was used. Unless otherwise indicated, the CHO cell line was cultured using α-MEM medium (Invitrogen) containing 10% dialyzed fetal bovine serum (TRA Thermo Electron).

The cells cultured to nearly confluent were rinsed with PBS (Invitrogen) on the previous day of the assay, peeled off with EDTA (0.5 μM, Wako Junyaku) and recovered by centrifugation. The number of the obtained cells was counted, and the cells were diluted such that 3×10$^5$ cells were contained per 1 mL of the medium, dispensed to a 96 well black clear bottom plate (coaster) by 100 μL per well and cultured overnight in a CO$_2$ incubator. Various test compounds were added to the CHO cells thus prepared, and the changes in the intracellular calcium concentration were measured using FLIPR (Molecular Device). The below-mentioned pre-treatment was applied to measure changes in the intracellular calcium concentration by FLIPR.

As an assay buffer, for adding a fluorescence dye Fluo3-AM (Molecular Device) to the cells, α-MEM medium supplemented with fatty acid free BSA to a final concentration of 0.1% was prepared. A fluorescence dye solution was prepared by adding 500 μM probenecid dissolved in 1N NaOH to the assay buffer to a final concentration of 2.5 μM, and adding the solution (10 mL) to 1 vial of component A (Molecular Device). One day before the assay, the medium of CHO cells re-plated on a 96 well black clear bottom plate was removed, and the cells were washed with D-PBS(−). Thereto was added 50 μL of an assay buffer (α-MEM medium supplemented with fatty acid free BSA to a final concentration of 0.1%), and the cells were cultured in a $CO_2$ incubator at 37° C. for 60 min. Then, the fluorescence dye solution was dispensed by 100 μL per well, and the cells were cultured in a $CO_2$ incubator for 1 hr to allow uptake of the fluorescence dye by the cells.

During this period, the test compound was diluted to a given concentration with the assay buffer, and dispensed to a polypropylene 96-well plate (sample plate) by 100 μL. The cell plate and the sample plate were simultaneously set on FLIPR. After the above-mentioned pre-treatment, variation in the intracellular calcium concentration after addition of various test compounds (50 μL) was measured by FLIPR. Based on the results, the agonist activity of each compound (1 μM) was calculated as a relative activity value with the activity of 10 μM γ-linolenic acid (GPR40 agonist) as 100%. The results are shown in Table 1.

TABLE 1

| Compound No. | Relative activity value |
|---|---|
| Example 2 | 111 |
| Example 3 | 103 |
| Example 5 | 108 |
| Example 7 | 119 |
| Example 9 | 99 |
| Example 11 | 114 |
| Example 13 | 109 |
| γ-linolenic acid | 100 |

INDUSTRIAL APPLICABILITY

Compound (I) and a prodrug thereof have a superior GPR40 receptor function modulating action, and can be used as agents for the prophylaxis or treatment of diabetes and the like.

This application is based on application No. 2005-222010 filed in Japan, the contents of which are incorporated hereinto by reference.

The invention claimed is:

1. A compound represented by the formula:

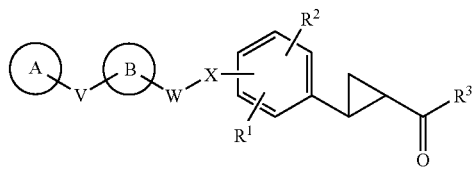

[I]

wherein
ring A is an optionally substituted cyclic group;
ring B is an optionally substituted ring;
V is a bond or a spacer having 1 to 3 atoms in the main chain;
W is an optionally substituted $C_{1-6}$ alkylene group;
X is O or S;
$R^1$ and $R^2$ are the same or different and each is a hydrogen atom, a halogen atom, a $C_{1-6}$ alkyl group or a $C_{1-6}$ alkoxy group; and
$R^3$ is an optionally substituted hydroxy group or an optionally substituted amino group, provided that when V is a bond and W is a methylene group, then ring B should not be oxazole and thiazole,
or a salt thereof, excluding 2-(2-{[6-(benzyloxy)-2-naphthyl]methoxy}phenyl)cyclopropanecarboxylic acid.

2. A prodrug of the compound of claim 1.

3. The compound of claim 1, wherein ring B is an optionally substituted benzene ring.

4. The compound of claim 1, wherein ring A is an optionally substituted phenyl.

5. A compound of claim 1, wherein ring A is an optionally substituted thiazolyl.

6. The compound of claim 1, wherein V is
(1) a bond;
(2) —$W^3$—N($R^4$)—$W^2$—; or
(3) —$W^3$—O—$W^2$—
wherein
$W^2$ and $W^3$ are the same or different and each is a bond or an optionally substituted linear $C_{1-2}$ alkylene group, and when both of $W^2$ and $W^3$ are optionally substituted linear $C_{1-2}$ alkylene groups, then the total carbon number of the linear $C_{1-2}$ alkylene groups constituting $W^2$ and $W^3$ should be 2, and $R^4$ is a hydrogen atom or a substituent.

7. The compound of claim 1, wherein W is —$CH_2$—.

8. The compound of claim 1, wherein X is O.

9. The compound of claim 1, wherein $R^1$ and $R^2$ are each a hydrogen atom or a halogen atom.

10. The compound of claim 1, wherein $R^3$ is a hydroxy group.

11. A compound of claim 1, which is selected from
2-(4-{[4'-(2-ethoxyethoxy)-2',6'-dimethylbiphenyl-3-yl]methoxy}phenyl)cyclopropanecarboxylic acid,
2-[4-({4'-[(1,1-dioxidotetrahydro-2H-thiopyran-4-yl)oxy]-2',6'-dimethylbiphenyl-3-yl}methoxy)phenyl]cyclopropanecarboxylic acid,
2-[4-({2',6'-dimethyl-4'-[(3-methyloxetan-3-yl)methoxy]biphenyl-3-yl}methoxy)phenyl]cyclopropanecarboxylic acid,
2-[4-[((3-methylbutyl)(4-[4-(trifluoromethyl)phenyl]-1,3-thiazol-2-yl}amino)methyl]benzyl}oxy)phenyl]cyclopropanecarboxylic acid,
2-[4-({4-[(propyl(4-[4-(trifluoromethyl)phenyl]-1,3-thiazol-2-yl}amino)methyl]benzyl}oxy)phenyl]cyclopropanecarboxylic acid,
and salts thereof.

12. An insulin secretagogue comprising the compound of claim 1 or a prodrug thereof.

13. A pharmaceutical agent comprising the compound of claim 1 or a prodrug thereof.

14. An agent for the treatment of diabetes, which comprises a compound of claim 1 or a prodrug thereof.

15. The pharmaceutical agent of claim 13, which is an agent for the treatment of diabetes.

16. A method of promoting insulin secretion in a mammal, which comprises administering an effective amount of the compound of claim 1 or a prodrug thereof to the mammal.

17. A method for the treatment of diabetes in a mammal, which comprises administering an effective amount of a compound of claim 1 or a prodrug thereof to the mammal.

* * * * *